(12) United States Patent
Salem

(10) Patent No.: US 10,998,092 B2
(45) Date of Patent: May 4, 2021

(54) DISPENSER APPARATUS

(71) Applicant: Mores, Inc., Burbank, CA (US)

(72) Inventor: Ayman Salem, Burbank, CA (US)

(73) Assignee: Mores, Inc., Burbank, CA (US)

( * ) Notice: Subject to any disclaimer, the term of this patent is extended or adjusted under 35 U.S.C. 154(b) by 110 days.

(21) Appl. No.: 14/952,547

(22) Filed: Nov. 25, 2015

(65) Prior Publication Data

US 2016/0078708 A1     Mar. 17, 2016

Related U.S. Application Data

(63) Continuation-in-part of application No. 14/080,021, filed on Nov. 14, 2013, now Pat. No. 9,747,417.

(51) Int. Cl.
| | |
|---|---|
| *G16H 20/13* | (2018.01) |
| *G07F 17/00* | (2006.01) |
| *B65D 83/04* | (2006.01) |
| *A61J 7/00* | (2006.01) |
| *G16H 20/30* | (2018.01) |
| *G16H 20/60* | (2018.01) |
| *G16H 20/70* | (2018.01) |
| *G16H 40/67* | (2018.01) |

(52) U.S. Cl.
CPC ............ *G16H 20/13* (2018.01); *A61J 7/0069* (2013.01); *B65D 83/0445* (2013.01); *G07F 17/0092* (2013.01); *A61J 7/0076* (2013.01); *G16H 20/30* (2018.01); *G16H 20/60* (2018.01); *G16H 20/70* (2018.01); *G16H 40/67* (2018.01)

(58) Field of Classification Search
CPC ............ G16H 20/13; G07F 17/0092; B65D 83/0445; A61J 7/0069
USPC .......................................... 709/217
See application file for complete search history.

(56) References Cited

U.S. PATENT DOCUMENTS

| | | | | |
|---|---|---|---|---|
| 5,431,491 A | * | 7/1995 | Melgaard | G01R 31/2868 312/223.1 |
| 5,671,198 A | * | 9/1997 | Tsuchiya | G11B 17/30 369/30.32 |
| 6,213,403 B1 | * | 4/2001 | Bates, III | G06K 19/0718 235/486 |

(Continued)

*Primary Examiner* — Vivek Srivastava
*Assistant Examiner* — Hien V Doan
(74) *Attorney, Agent, or Firm* — Smyrski Law Group, A P.C.

(57) ABSTRACT

A dispenser apparatus is presented, the dispenser apparatus including a central opening, a display, an advancing mechanism configured to advance at least one prescription tray vertically through the central opening of the dispenser apparatus, and an ejection mechanism configured to eject one prescription tray from the dispenser apparatus. The dispenser apparatus may be configured to interface with a personal care system including a personal care combination display/mirror device comprising a surface operating as a reflective surface and a plurality of connection ports, each connection port configured to receive a hardware personal care module, each hardware personal care module including software facilitating performance of at least one personal care function and configured to interact with the personal care combination display/mirror device to facilitate personal care of a user, wherein personal care comprises at least one of health, fitness, wellness, fashion, cosmetics, and pharmaceuticals.

18 Claims, 19 Drawing Sheets

(56) References Cited

U.S. PATENT DOCUMENTS

| | | | | |
|---|---|---|---|---|
| 2002/0147526 | A1* | 10/2002 | Siegel | A61J 7/0481 |
| | | | | 700/237 |
| 2006/0058724 | A1* | 3/2006 | Handfield | G07F 9/026 |
| | | | | 604/20 |
| 2007/0159316 | A1* | 7/2007 | Mischel, Jr. | A47G 1/02 |
| | | | | 340/461 |
| 2008/0004748 | A1* | 1/2008 | Butler | G06Q 30/02 |
| | | | | 700/244 |
| 2011/0054936 | A1* | 3/2011 | Cowan | G06F 19/322 |
| | | | | 705/3 |
| 2011/0168733 | A1* | 7/2011 | Yuyama | G07F 17/0092 |
| | | | | 221/1 |
| 2013/0002795 | A1* | 1/2013 | Shavelsky | A61J 7/04 |
| | | | | 348/14.01 |
| 2014/0173269 | A1* | 6/2014 | Varoglu | H04L 51/18 |
| | | | | 713/150 |
| 2015/0174392 | A1* | 6/2015 | Stringdahl | A61B 5/6833 |
| | | | | 607/48 |

* cited by examiner

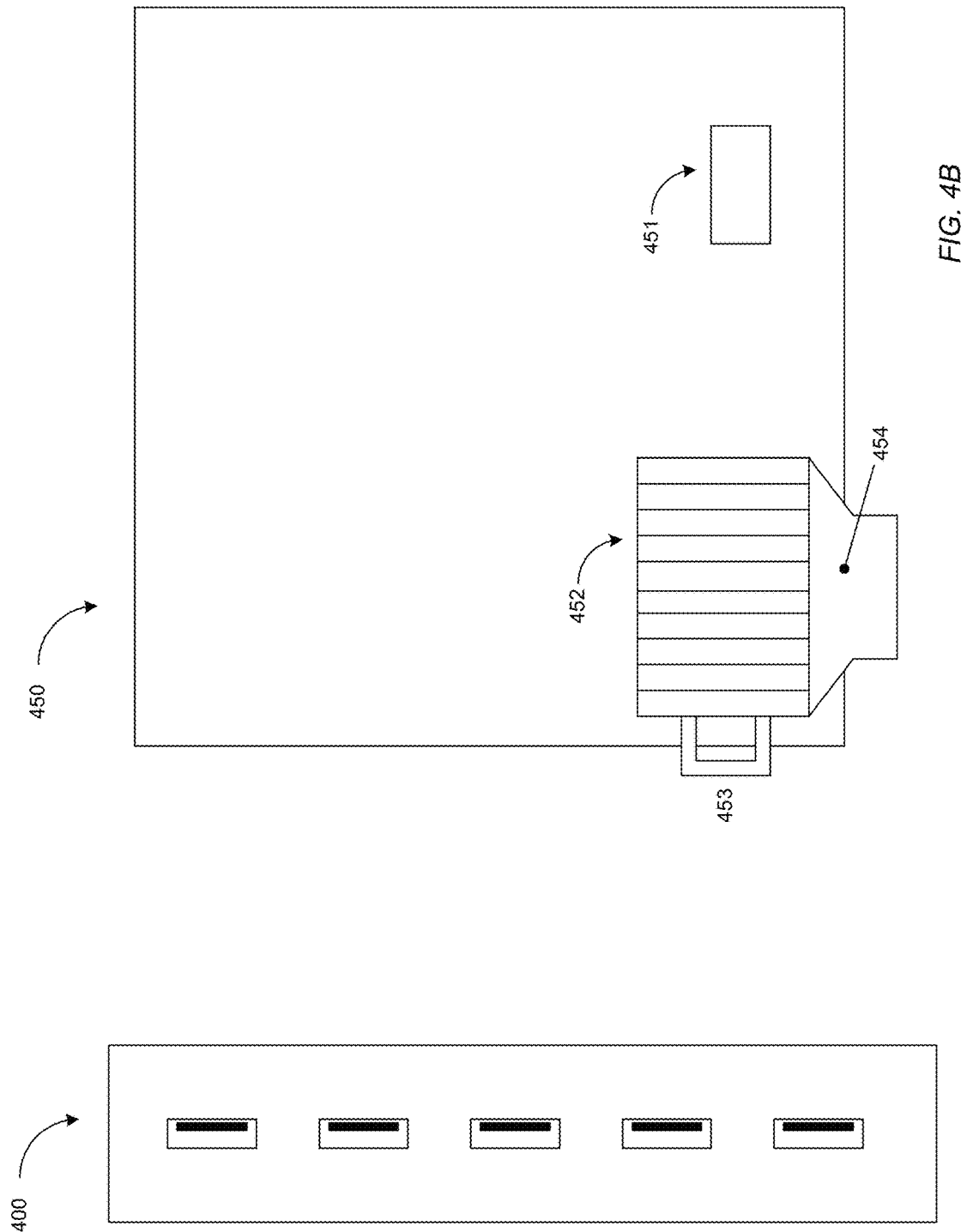

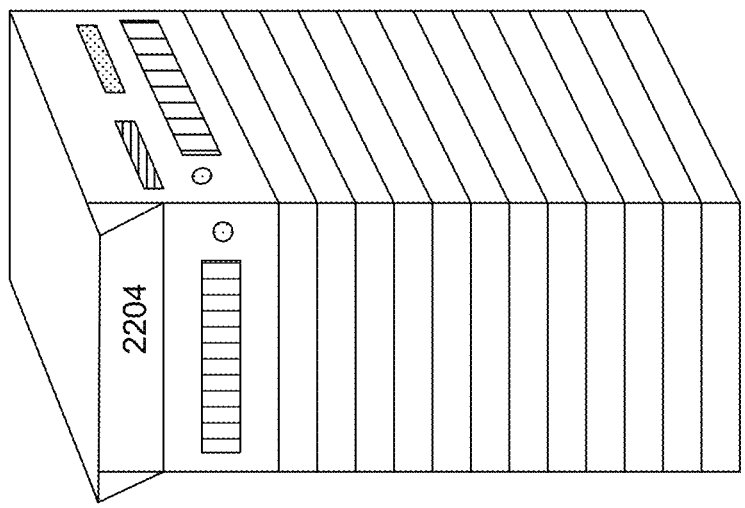
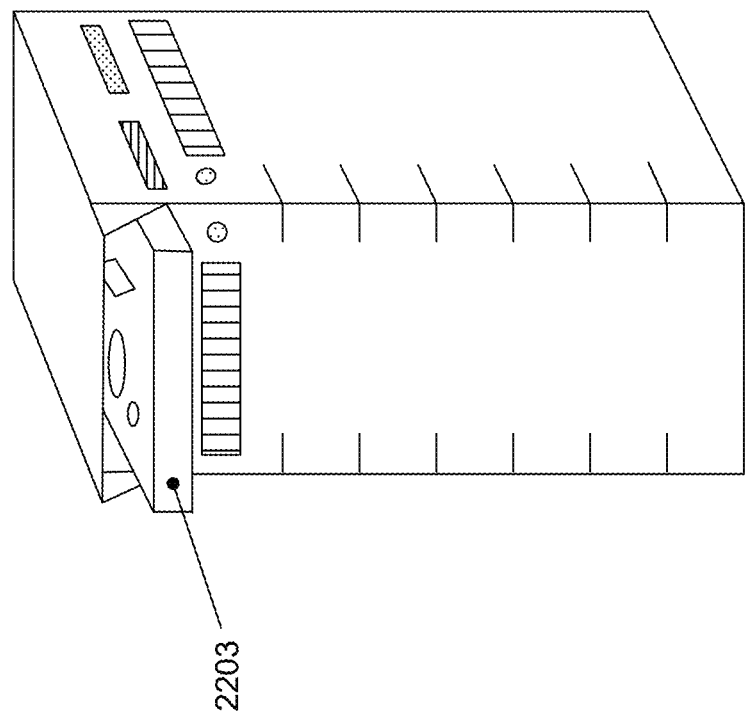
FIG. 22

DISPENSER APPARATUS

The present application is a continuation-in-part of co-pending U.S. patent application Ser. No. 14/080,021, inventor Ayman Salem, entitled "Method and Apparatus for Enhanced Personal Care," filed Nov. 14, 2013, the entirety of which is incorporated herein by reference.

BACKGROUND OF THE INVENTION

Field of the Invention

The present invention relates in general to personal care, and more specifically enabling a user to monitor, assess, maintain, receive, and track information to actively improve personal care and lifestyle attributes, including but not limited to user health, physical appearance, fashion, fitness/sports, cosmetics and wellness.

Description of the Related Art

People seek to improve or at least maintain their personal care on a daily basis. Whether monitoring their own personal health, appearance, fitness/sports, or wellness, for example, people purchase and use an array of products and services. In the area of health care and maintenance alone, people may be taking a series of medications, may need to be monitored on a regular basis for a condition, may have an injury that needs to be evaluated for progress, and so forth. Each of these wellness tasks requires a different product or service. An individual may need to make a trip to a physician, then to a pharmacist to obtain a prescription, may need to purchase over-the-counter health care products, and may require a long term care giver to provide necessary personal care. At a later time, the individual may need to obtain further products or services—sometimes as frequently as on a daily basis.

Other areas of personal care, such as cosmetics, wardrobe and so forth, also require a series of products and/or services, and in some instances recommendations or decisions, to carry out and achieve a desired level of personal care. People have previously needed to locate and then obtain all necessary personal care products and services from a myriad of sources, typically requiring traveling to multiple locations, making purchases from several web sites, and/or generally spending a great deal of time and effort to maintain their personal appearance and well-being. In some instances, the desired product or service can be difficult or impossible to obtain due to mass production constraints or other. Therefore industry products are not personalized as such.

Further, previous devices do not offer an ability to track information in an efficient manner, namely information associated with the personal care requirements of the individual in a manner that can be relatively easily navigated and can be utilized by the user to facilitate and/or improve his or her personal care.

Another issue with currently available equipment is the ability to track patient/user vital signs and information and when appropriate, administer beneficial treatments to the patient/user. A further issue is the ability to administer medications in a controlled and convenient manner, with connection to a central system.

Further, standards of healthcare delivery are strictly adhered to at a medical facility or a doctor's office, while consumers or patients at home are totally left to their own, leading to a fragmented healthcare delivery loop with high costs shouldered by all participants. Closing the loop and bridging the fragmented portion at home with a robust home care and personal wellness system may have positive personal and societal impacts.

It would be highly beneficial if multiple aspects of personal care could be obtained from a readily accessible system or device, where such a system could provide personalized care directed to the specific needs or desires of an individual user.

SUMMARY OF THE INVENTION

According to one aspect of the present design, there is provided a dispenser apparatus comprising a central opening, a display, an advancing mechanism configured to advance at least one prescription tray vertically through the central opening of the dispenser apparatus, and an ejection mechanism configured to eject one prescription tray from the dispenser apparatus.

According to a second aspect of the present design, there is provided a prescription tray dispensing apparatus comprising an outer enclosure surrounding a central opening, the outer enclosure sized to accommodate a prescription tray, a display, an advancing mechanism configured to advance the prescription tray vertically through the central opening within the outer enclosure of the prescription tray dispensing apparatus, and an ejection mechanism configured to eject the prescription tray from the prescription tray dispensing apparatus.

According to a further embodiment of the present design, there is provided a dispenser apparatus configured to interface with a personal care system, the dispenser apparatus comprising an enclosure surrounding a central opening, a display, an advancing mechanism configured to advance at least one prescription tray vertically through the central opening of the dispenser apparatus, and an ejection mechanism configured to eject one prescription tray from the dispenser apparatus. The personal care system comprises a personal care combination display/mirror device comprising a surface operating as a reflective surface and a plurality of connection ports, each connection port configured to receive a hardware personal care module, each hardware personal care module comprising software facilitating performance of at least one personal care function and configured to interact with the personal care combination display/mirror device to facilitate personal care of a user, wherein personal care comprises at least one of health, fitness, wellness, fashion, cosmetics, and pharmaceuticals.

These and other advantages of the present invention will become apparent to those skilled in the art from the following detailed description of the invention and the accompanying drawings.

BRIEF DESCRIPTION OF THE DRAWINGS

For a more complete understanding of the present disclosure, reference is now made to the following figures, wherein like reference numbers refer to similar items throughout the figures:

FIG. 4A illustrates a side view of a device similar to that shown in FIG. 2;

FIG. 4B is a rear view of an embodiment of the device;

FIG. 22 shows alternate representations of the dispenser apparatus used with the prescription tray(s) disclosed.

The exemplification set out herein illustrates particular embodiments, and such exemplification is not intended to be construed as limiting in any manner.

DETAILED DESCRIPTION OF THE INVENTION

The following description and the drawings illustrate specific embodiments sufficiently to enable those skilled in the art to practice the system and method described. Other embodiments may incorporate structural, logical, process and other changes. Examples merely typify possible variations. Individual components and functions are generally optional unless explicitly required, and the sequence of operations may vary. Portions and features of some embodiments may be included in or substituted for those of others.

In general, the present invention includes personal care system that employs modular hardware configured to offer personal care information, products, and services directed to a specific user. The present design may take the form of a device including a mirror having processing and communication capability and configured with a plurality of connection points, the connection points allowing personal care modules to be connected to the device. Additional functionality may be provided with the mirror in a central or main hardware component. In this manner, an individual can maintain a device at her residence or place of work or elsewhere that can be configured to meet her personal care needs.

The system may include a portable device configured to be taken with the user, while traveling locally or long distance, and connect with the base device such that the user may record desired information and provide the information to the base location at a later time.

Additionally, the present system may include a communications network, which may be server or cloud based, wherein the user can store personal care information, obtain personal care information such as recommendations specific to the user, may schedule and receive reminders, and so forth.

Figure 1:
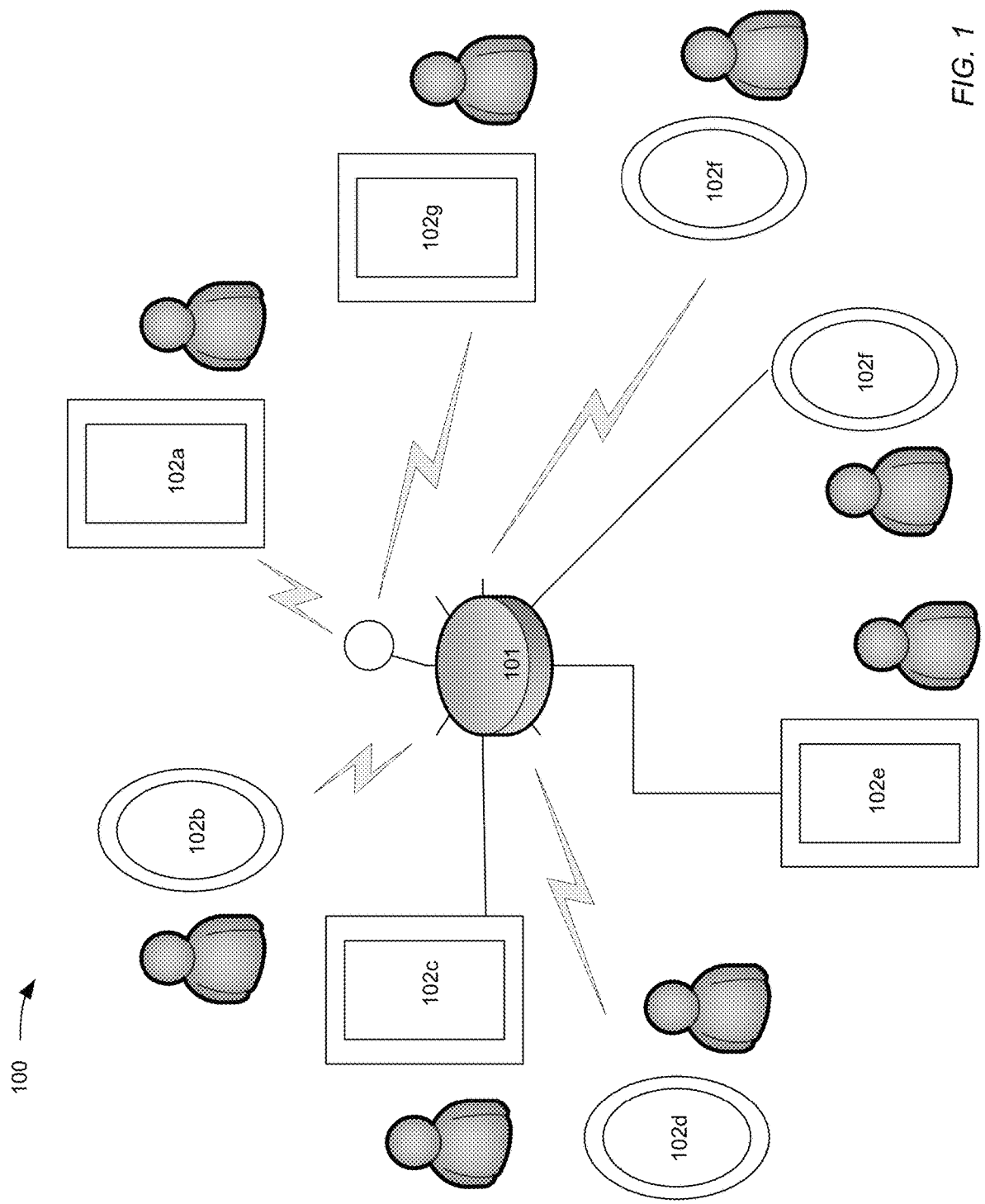
FIG. 1 is a general system overview of the present design.

FIG. 1 is a general system overview of the present design. From FIG. 1, network 100 includes a processing and storage site 101, also referred to as a remote device arrangement herein, configured to communicate with and receive communications from personal care devices 102a-h. Communication may be effectuated between the processing and storage site 101 and the personal care devices 102a-h in any manner known and available, including but not limited to internet connectivity via wire, wireless (802.11a/b/n/g, Wifi), cellular, and or other communication means. While a single processing and storage site 101 is shown, it is to be understood that more than one such site may be employed and more than one such site may carry out some of the functionality disclosed herein.

In general, information about an individual's personal care may be obtained at a personal care device, e.g. personal care device 102b, and this information may be communicated to processing and storage site 101. Information about personal care generally falls into five categories, but other categories may be employed or provided, the five categories including health, fitness/wellness, fashion, cosmetics, and pharmaceuticals. While personal care device 102b may offer such capabilities, a user may or may not employ all capabilities. A user may simply wish to employ the present design for health purposes. Information obtained may be manually entered by the user or obtained using a set of readings or information obtained at the device, and/or information may be provided to the personal care device 102b from the processing and storage site. As an example, blood pressure readings may be made by the user using the personal care device, the blood pressure information may be provided from the personal care device 102b to the processing and storage site 101, and the processing and storage site 101 may provide a recommendation back to the user, even something as innocuous as "You have a slightly elevated blood pressure. The following may be potential meal suggestions for the coming days." As may be understood, any type of interaction between the user, user device 102b, and processing and storage site 101 may be employed as desirable, such as determining the user's body type and recommending clothing for the user, determining skin tone and making a recommendation for particular skin care and/or cosmetic purchases, and so forth.

Figure 2A:
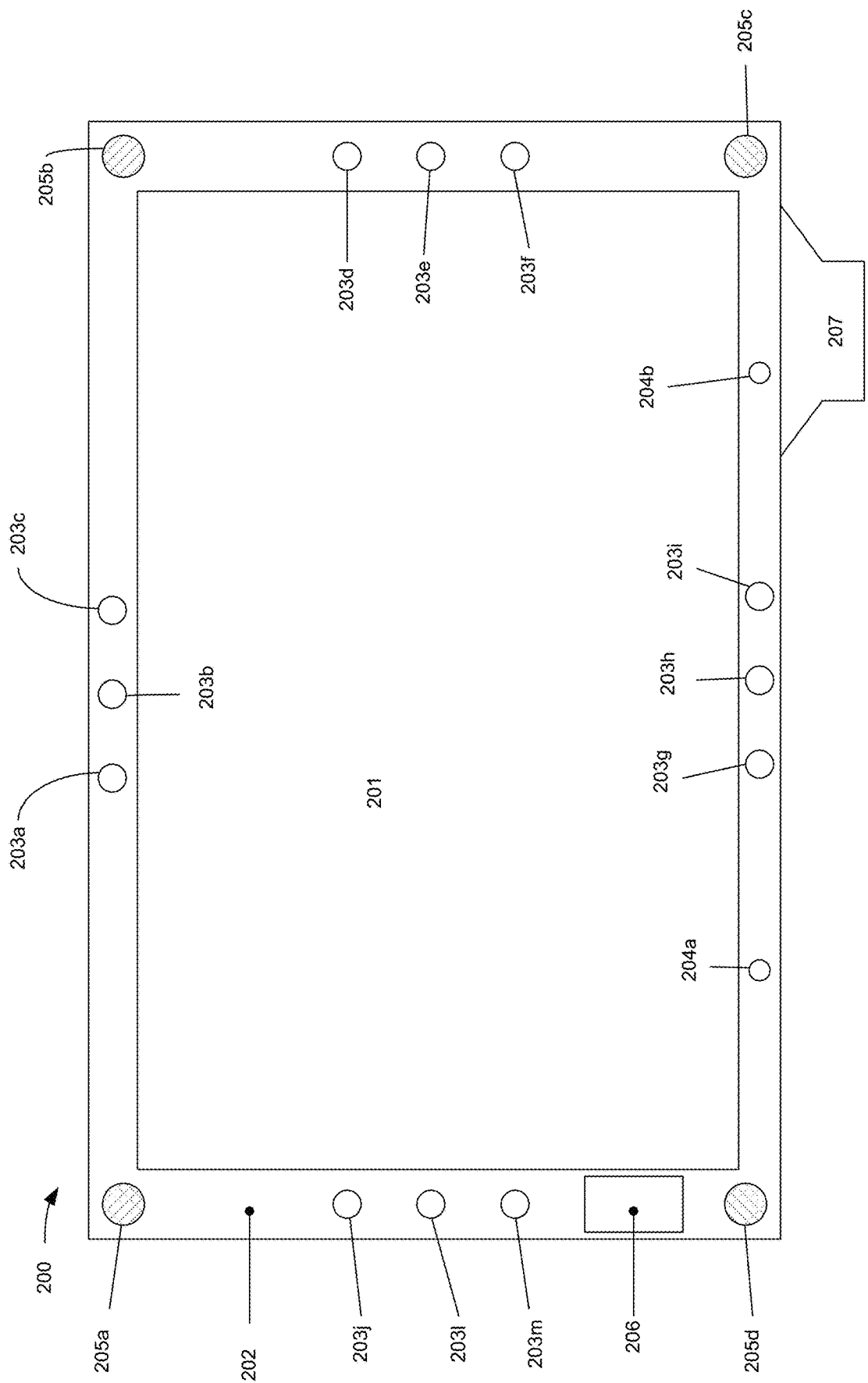
FIG. 2A illustrates a rectangular embodiment of one aspect of the present design.

One embodiment of the present design is presented in FIG. 2A. The device 200 includes a central element 201, typically a mirror that operates as a display screen as well. Such devices are available from, for example, Ox-Home (ox-home.com) or Samsung, with the Samsung product called the LED mirror TV. Edge element 202 may be provided and made from any suitable material, and shown in FIG. 2A are cameras 203a-1, microphones 204a and 204b, speakers 205a-d, and sensor, voice, or fingerprint reader 206. The sensor may be any type of sensor (biometric, heat, or otherwise), and a voice recognition component may be present, operating separately or using microphones 204a and 204b together with voice recognition software. Also shown in this view is an optional pill dispenser tray 207. While a certain number of components are shown in FIG. 2A, it is to be understood that any number of components may be employed and the invention is not so limited.

The user may stand in front of device 200 and view her reflection. She may verify her identity using fingerprint reader 206, where fingerprint reader 206 may connect to a processor as discussed below and may be able to verify a user's identity. Device 200 may photograph or visually record the user using one or more of cameras 203a-1. The user may speak words that may be received by microphones 204a and 204b, and the device 200 may speak words or provide audio information using speakers 205a-d.

Not shown in FIG. 2A is a series of connection slots in the device, typically in the FIG. 2A embodiment positioned on the outer edges of the device. The connection slots enable the user to connect modules having specialized functionality to the device for the purpose of facilitating personal care. A user can plug one or more modules into the device and can obtain desired functionality at a given point in time, such as a module to determine blood pressure, to determine weight (e.g. a connection to a scale), determine glucose level, and/or to track physical activity, among other functions. One example of connection slots in the device is a USB (Universal Serial Bus) connection, but any type of connectivity may be provided. For example, the device 200 may include a receiver or transceiver while a remote device or module may include a transmitter or transceiver, or the device 200 may include a connection slot for a receiver or transceiver, with connectivity to the device 200 provided via a slot, such as a USB slot.

Device 200 may provide wireless or wired connectivity, including reception of wireless signals or transmission of wireless signals, and may offer any other type of connectivity to a remote computing device as may be known in the art.

Figure 2B:
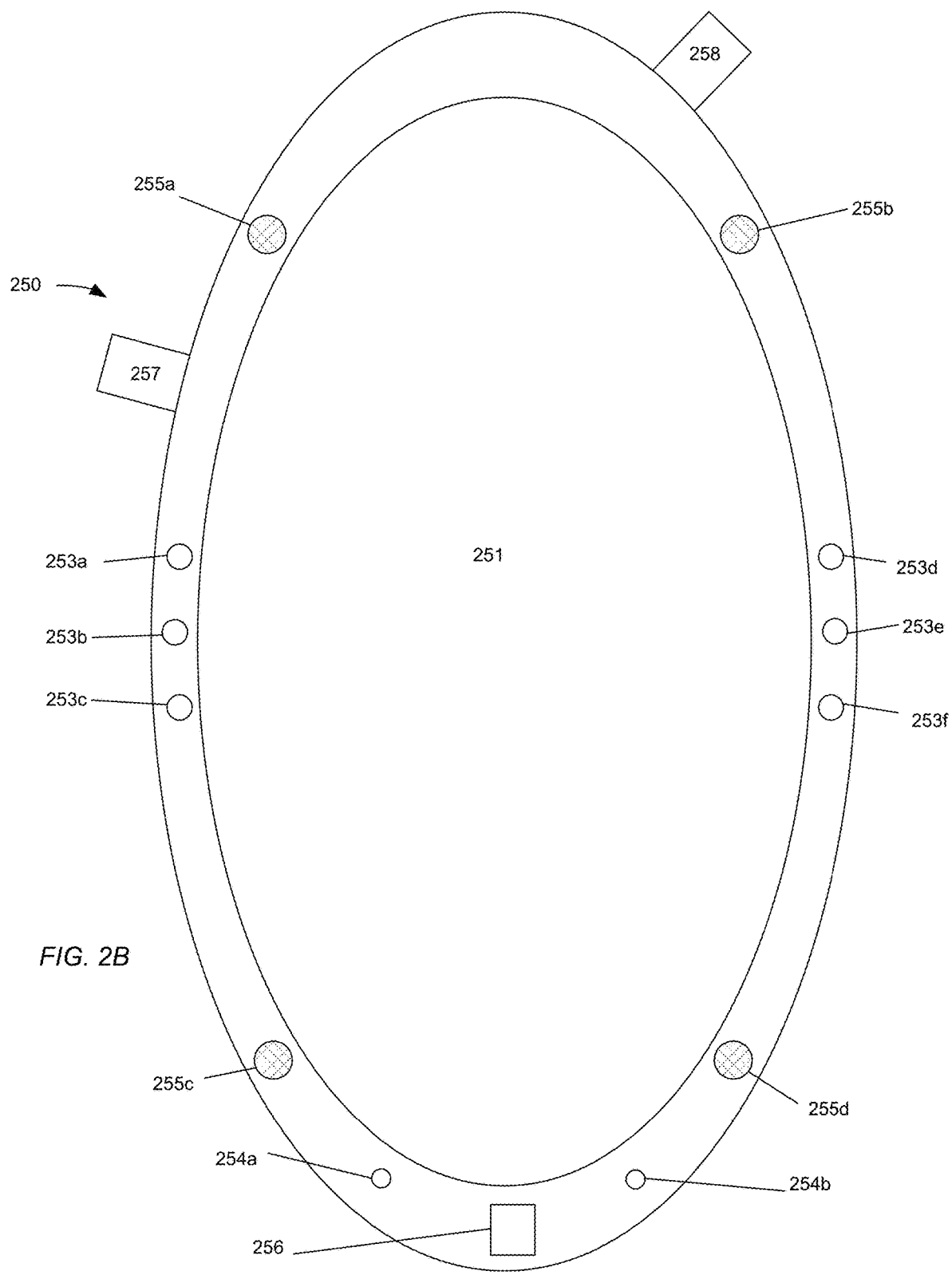
FIG. 2B illustrates an oval embodiment according to another aspect of the present design.

FIG. 2B illustrates an alternate embodiment of the device. The device 250 in the FIG. 2B embodiment is oval in shape, again with a central screen 251 that is both a mirror and a display. Edge element 252 may be provided and made from any suitable material, and cameras 253a-f, microphones 254a and 254b, speakers 255a-d, sensor, voice, or fingerprint reader 256 are provided. Also shown in this embodiment are two modules 257 and 258, each providing functionality as described herein. While a generally rectangular and a generally oval shape device is shown in FIGS. 2A and 2B, any form or type of device that provides the functionality described may be provided.

While shown as an integrated device in FIGS. 2A and 2B, it is to be understood that the present design may also include a conversion kit that may employ a plasma or LCD/LED television, including an outer frame that will be able to attach to the central screen and may include cameras, USB outlets and hardware such as a processor, storage, internet connectivity, and/or other pertinent functional components. A program may be provided that allows the user's television to operate in the manner discussed herein. Further, the present device may be incorporated into a piece of furniture, or into a wall, or into any type of other apparatus, either using the full device such as the embodiments shown in FIGS. 2A and 2B or as the aforementioned kit or part of the kit. The device may in various instances be mounted to a wall using mounting hardware known in the art.

Figure 3:
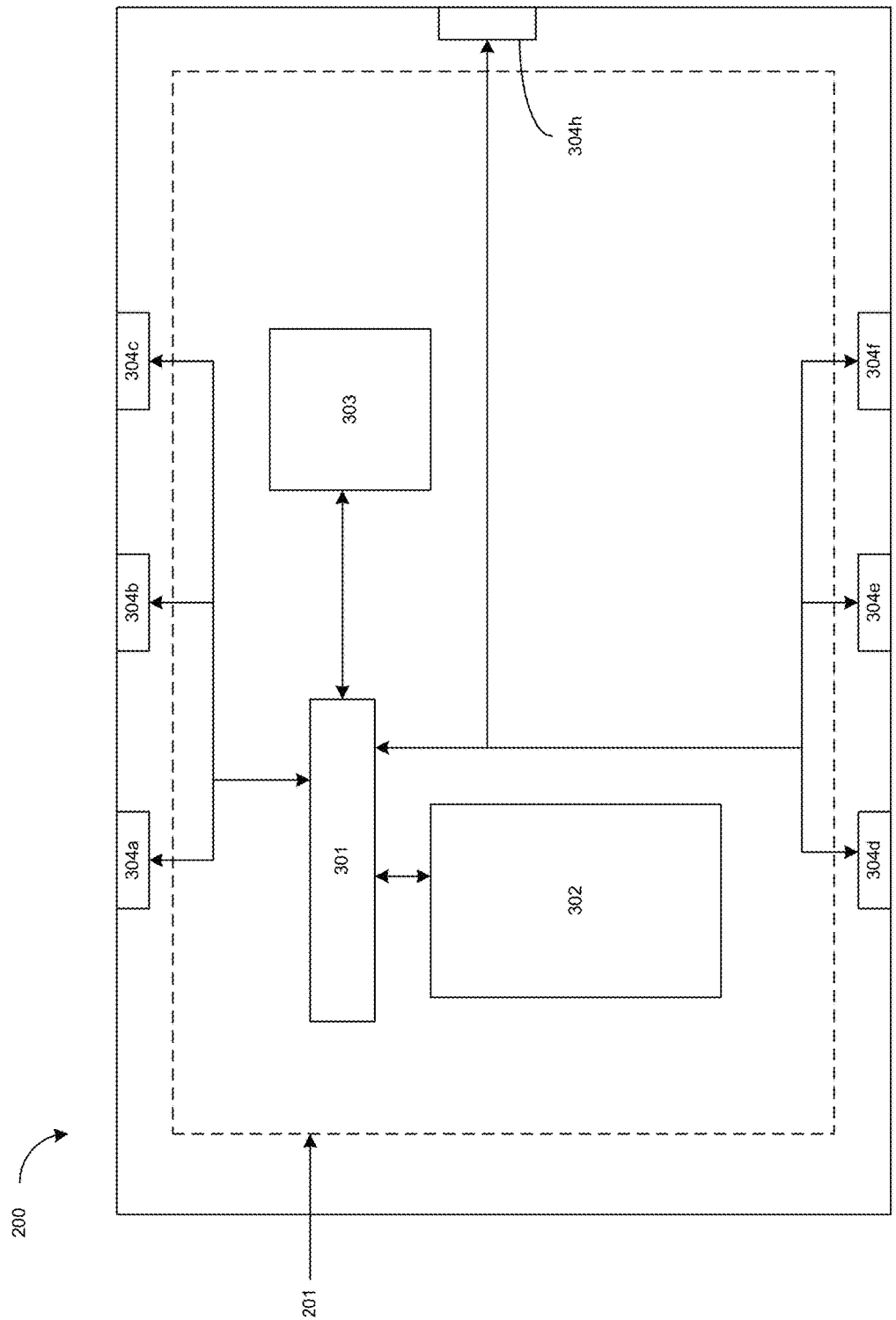
FIG. 3 is a general representation of certain components employed in the present design.

A general view of the electronics employed in the present design is shown in FIG. 3. From FIG. 3, device 200 includes a processor 301 connected to a storage device, such as a memory device 302, and is connected to display 201. The device may include wired or wireless connectivity, shown as element 303. Wireless signals may be transmitted from and received by the device and provided to the processor 301. Connections are provided to multiple connection slots, here shown as connection slots 304a-g. Any number of connection slots may be provided, and these may be USB slots or any type of connection to modules available in the art.

The device, such as device 200 or 250, may be open source in the sense that third parties may manufacture modules or module components that may interface with the device. Standards may be provided such that modules may be produced and desired functionality provided in conjunction with the device and its component parts. Further, the modules may be employed with devices already available, such as a blood pressure module used with an existing blood pressure cuff or other blood pressure evaluation apparatus.

FIG. 4A illustrates a side view of a device similar to that shown in FIG. 2A, where device 400 includes various openings or ports, such as USB ports, 402a-e. FIG. 4B is a rear view of an embodiment of the device 450, including an electrical connector 451 and a pill dispenser 452. The pill dispenser may be a removable feature and may be constructed to accept pills at a given time, with information provided to the processor as to how many and what type pills have been provided, and pills may be commanded to be dispensed by the processor, such as one pill per day if one pill per day is required. A handle 453 is provided such that the owner or some other individual can remove the dispenser or pull the dispenser out for purposes of restocking the dispenser. A tray 454 is provided such that pills or medications dispensed can be provided toward the front of the device and are easily accessible to the user.

Figure 5C:
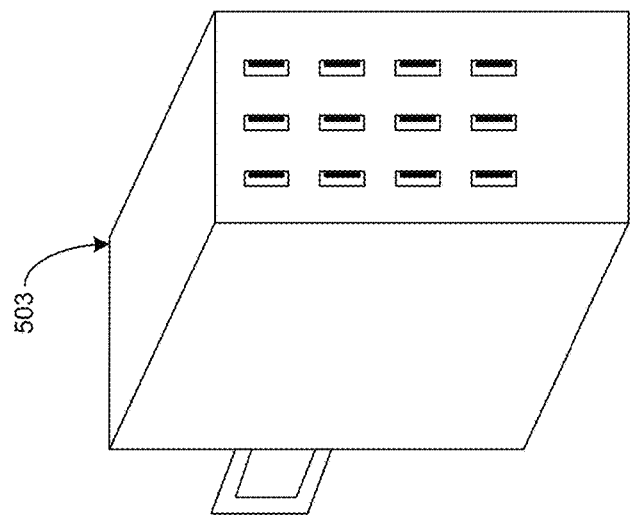
FIGS. 5A-5C illustrate apparatus including a set of separate USB receptacles that may be provided as an alternative to or in addition to the receptacles or slots provided on the device.
Figure 5B:
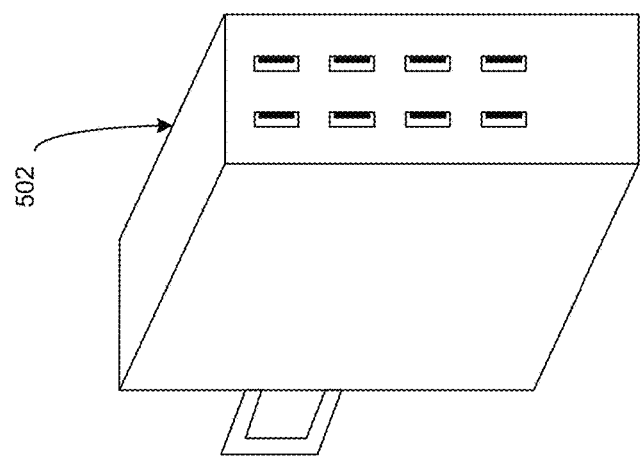
Figure 5A:
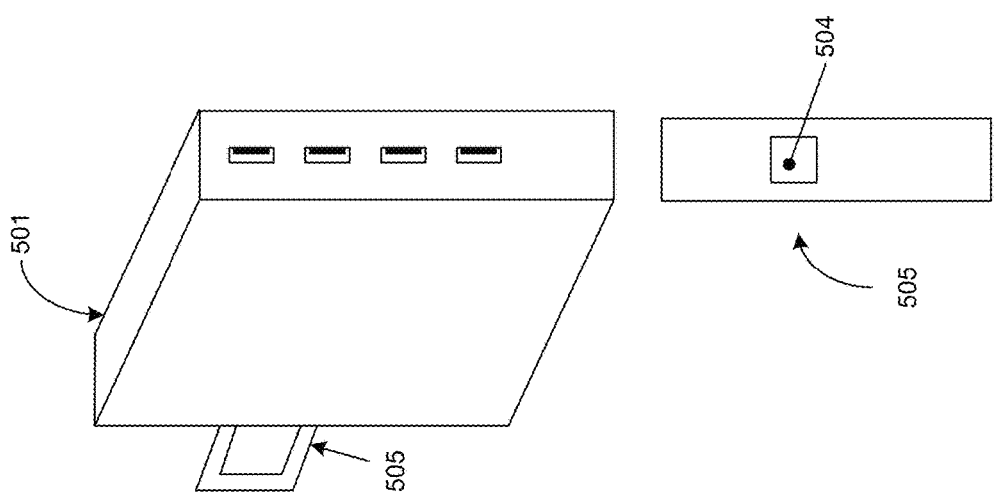

FIGS. 5A-5C illustrate apparatus including a set of separate USB receptacles that may be provided as an alternative to or in addition to the receptacles or slots provided on the device. The apparatus 501 of FIG. 5A, and the other apparatus 502 and 503 shown in FIGS. 5B and C, may be separate from the device and/or may connect to the device via wired or wireless communication. Apparatus 501 of FIG. 5A includes four ports or slots, apparatus 502 of FIG. 5B includes eight ports or slots, while apparatus 503 of FIG. 5C may include twelve ports or slots. Processing functionality may be provided in apparatus 501, 502, or 503, and the user may insert functional modules into the slots provided. Based on the module inserted, data may be collected, or data may be collected and transmitted to the device, such as device 200 in FIG. 2, for processing and/or further processing. As shown in bottom view 505 of FIG. 5A, a slot 504 may be provided for powering apparatus 501. The separate handheld unit described below may include port arrangements similar to those illustrated in FIGS. 5A to 5C, and a handle 505 or other carrying feature may be provided with the apparatus.

Figure 6:
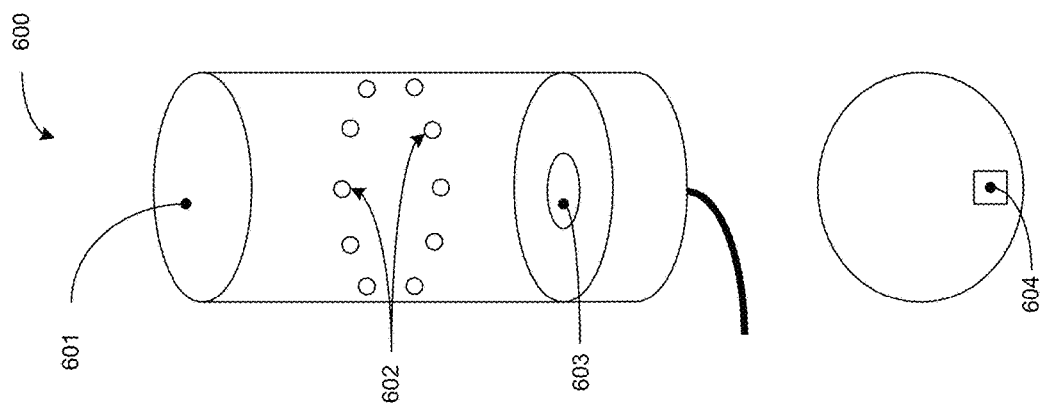
FIG. 6 illustrates an example of a magnification camera that may be employed with or provided as a module.

As may be appreciated, any number of functional personal care modules may be provided. As an example, devices to measure pulse rate, blood pressure, body temperature, and so forth may be provided, each with connectivity back to the device, such as device 200. FIG. 6 illustrates an example of a magnification camera 600 that may be provided for any number of uses, including but not limited to examining skin regions, oral examinations, and so forth. Magnification camera 600 includes an open area 601, a set of lights, such as LED (light emitting diode) and/or other lights of different wave lengths (e.g. ultraviolet or black light) employed 602 around the periphery of the interior of the magnification camera, and photographic element 603. The bottom view illustrates a port connection 604, such as a USB connection.

The device may be provided with a module or modules having an ability to read a barcode, including but not limited to a camera such as magnification camera 600. Any type of barcode or QR code or other code known in the art may be employed and may be read. Such scanning functionality enables the device to perform a variety of functions, including but not limited to reading prescription bottles, reading medical products, reading clothing tags and labels, reading cosmetics, reading containers of vitamins, and so forth.

Figure 7:
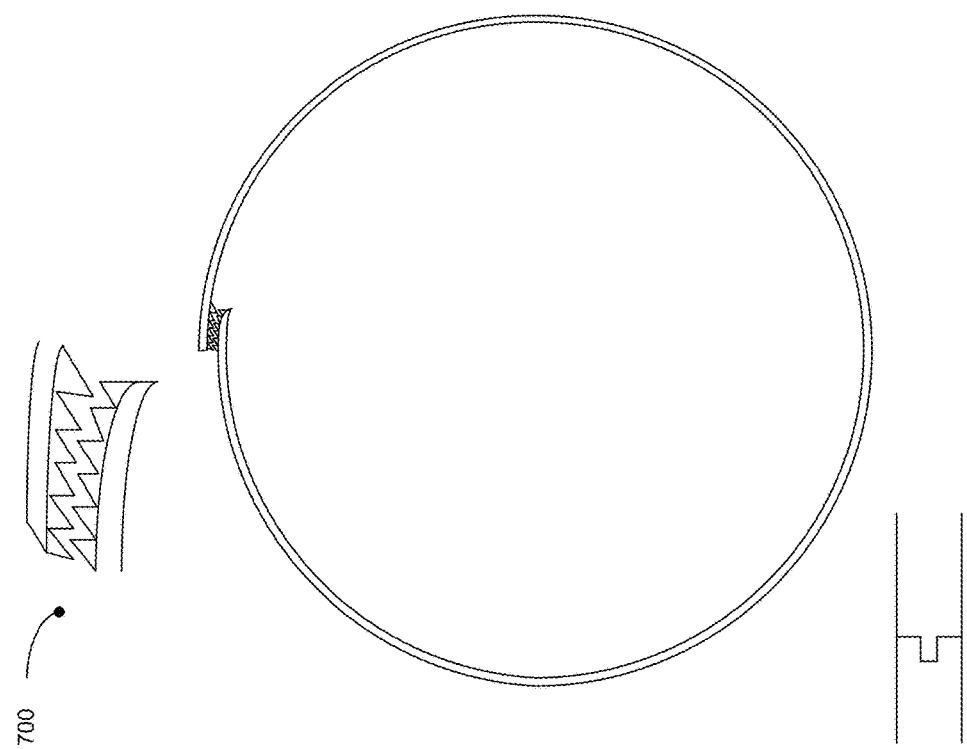
FIG. 7 illustrates an example of a sensing bracelet that may be employed with or provided as a module in accordance with the present design.
Figure 8:
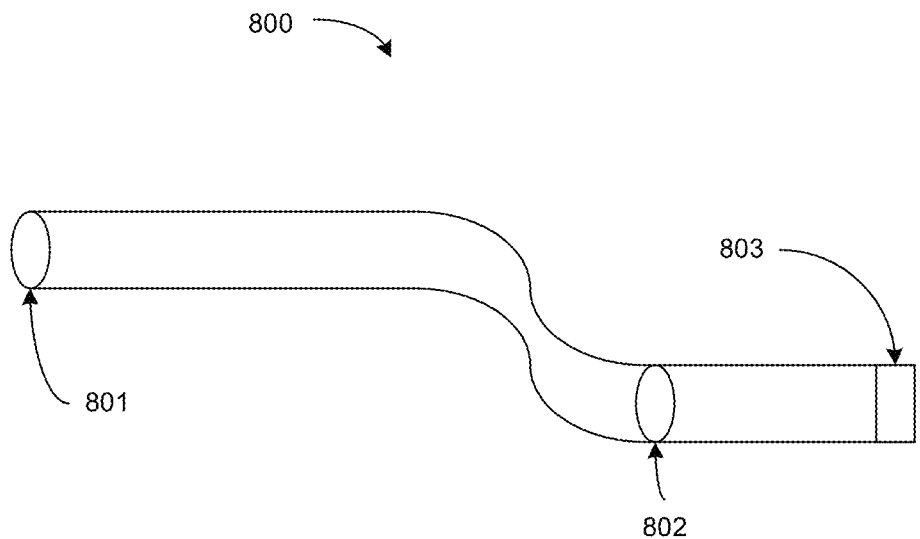
FIG. 8 illustrates a tape measure that may be employed as or in accordance with a module in the present design.

FIG. 7 illustrates an example of a sensing bracelet 700 that may be employed with a module in accordance with the present design. Sensing may be provided for pulse, temperature, and/or other pertinent measurements related to the individual. As an example, the sensing bracelet 700 may include lockable components such as teeth that enable resizing of the sensing bracelet 700. Sensing bracelet may also include a reflective coating or other marker enabling the device to sense the position of the bracelet and hence the user's arm. Such sensing capability may enhance the ability of the device to determine exercise performance and other pertinent information. FIG. 8 illustrates a tape measure 800 including a static reflective bead 801, an adjustable reflective bead 802, and a reflective position stop 803, enabling the measurement of anything, including but not limited to body parts, clothing, hair, separation of feet, and so forth. While FIGS. 7 and 8 do not include connections to modules or the main device, it is understood that such components may either be separate or may be connected by wire, or wirelessly (Bluetooth, etc.) to the device or a module as appropriate. In certain instances, minimal or no connection may be provided, such as no physical connection but an ability for the device, via microphone, camera, etc., to determine position of particular components. In FIG. 8, for example, tape measure 800 may not be connected by wire or wirelessly to a module or the device, but the device may employ a camera to determine positions of the static reflective bead 801, adjustable reflective bead 802, and/or reflective stop point 803 and use the measurement to determine the size of a desired object or objects.

Figure 9:
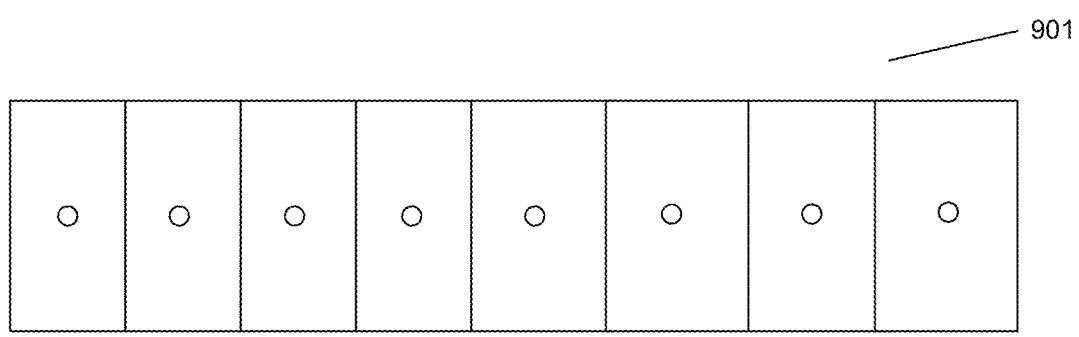
FIG. 9 is a reflective band or strap 901 that may be employed in association with a module.
Figure 11:
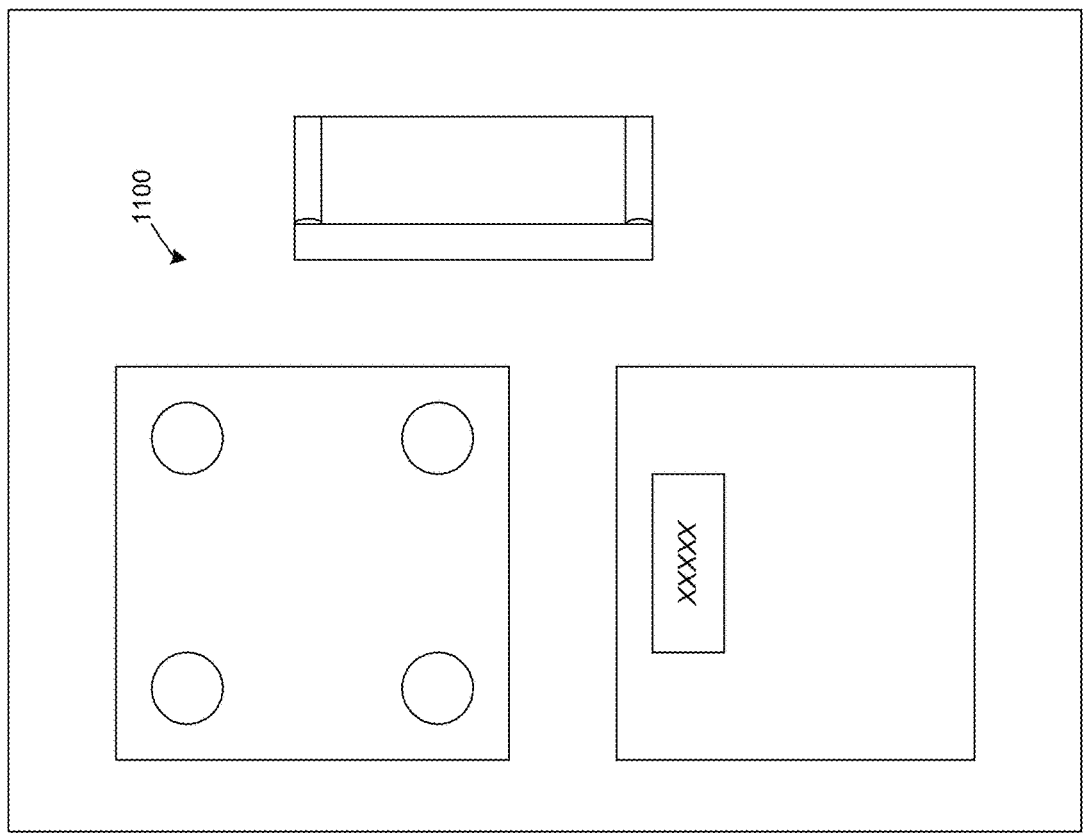
FIG. 11 illustrates a portable scale that may be used with the present design.
Figure 10:
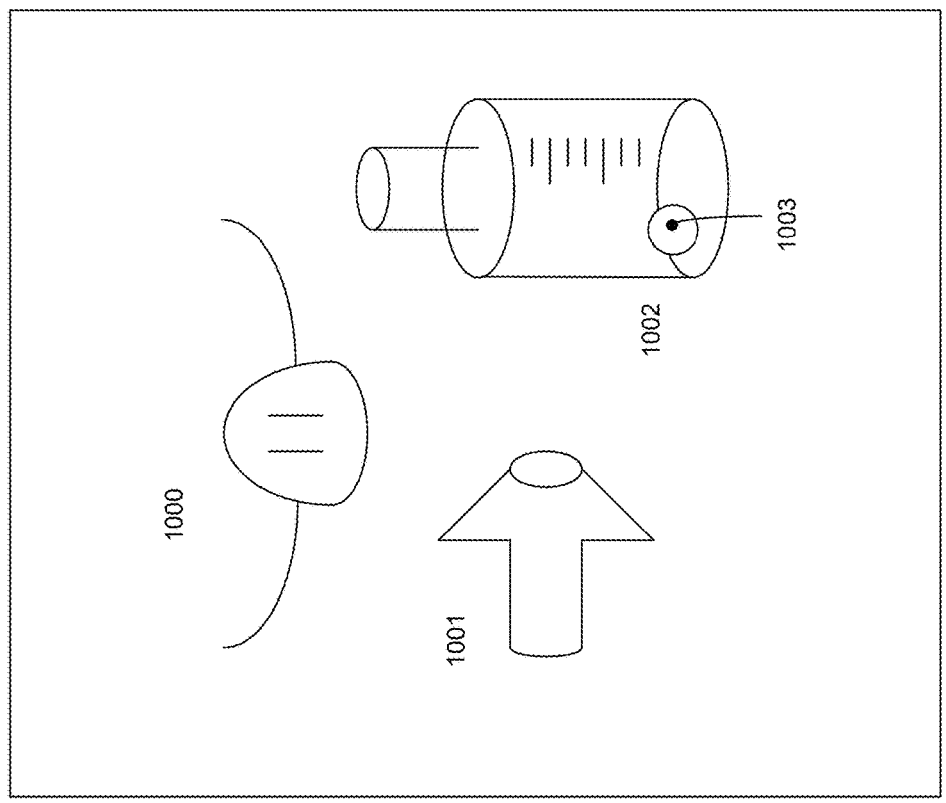
FIG. 10 shows a spirometer arrangement that may be employed as part of the present design.

FIG. 9 illustrates a reflective band or strap 901 that may be used to measure head parameters, including temperature, EEG, sweat, and so forth, and may include massage beads. Reflective measuring markers, such as lines or points, may be provided. FIG. 10 illustrates a spirometer 1000, mouthpiece 1001, and a bottle or container 1002 marked with measurement markings, typically reflective, and including a measurement ball 1003, also typically reflective. FIG. 11 illustrates a portable scale 1100, employed to weigh applicable items as well as acting as a turntable where a user can stand in front of the personal care device and the turn table rotates the individual to any desired degree of rotation needed. This can also be used as a base for an inflatable or non-inflatable mannequin of the user for purposes of digitizing garments of clothes, accessories or otherwise implementing physical organ changes on the mannequin prior to desired change on the consumer for example but no limited to the suggested sites of body part enhancements or wrinkles treatment with Botox.

Figure 12:
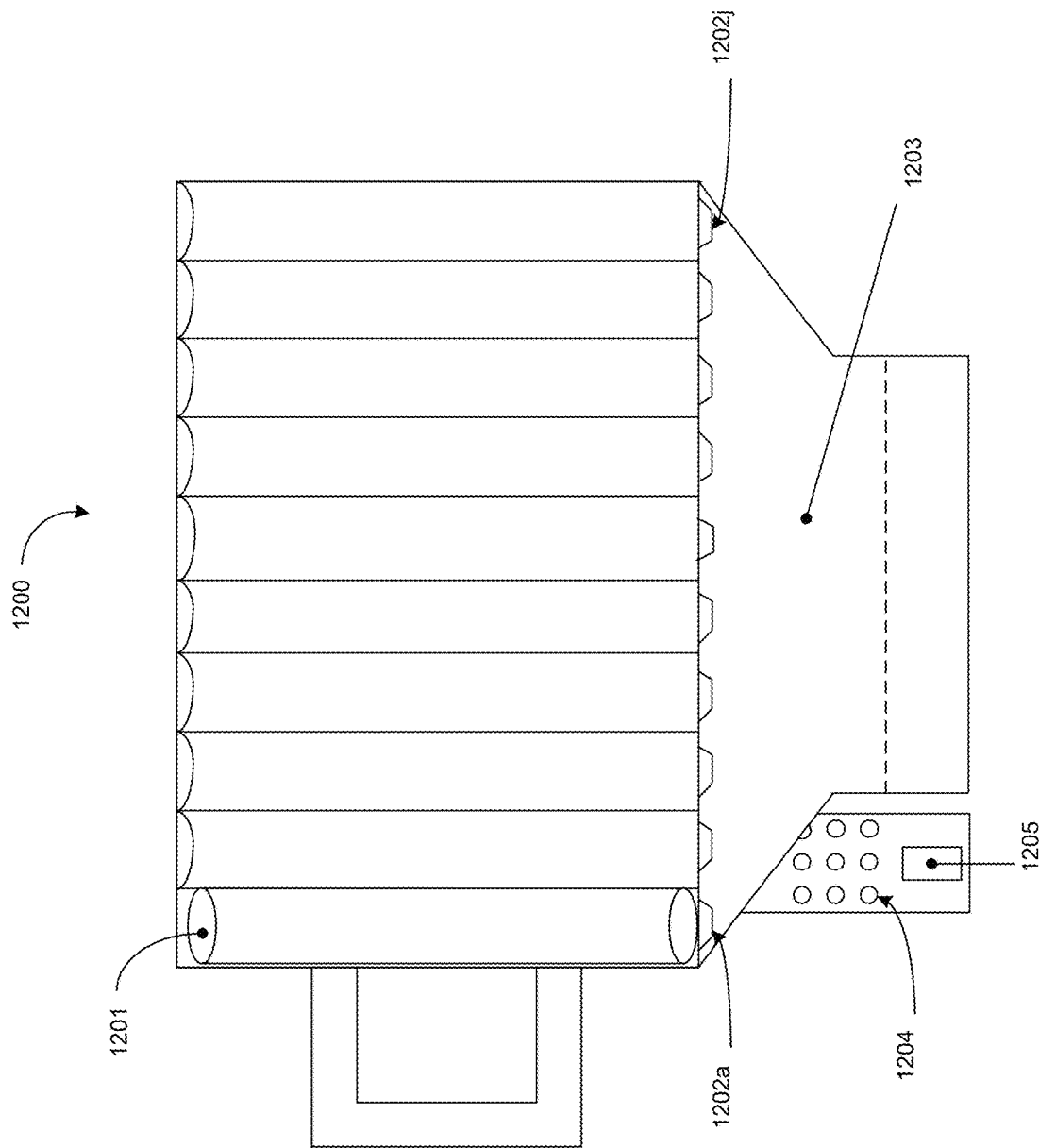
FIG. 12 is a pill dispenser that may be employed with the present design.

FIG. 12 illustrates a pill dispenser 1200, including a locked compartment 1201 for controlled substances, having programmable dispensing windows 1202a-g configured to control disbursement of pills, a tray or holder 1203, manual pill dispensing buttons 1204, and a fingerprint security reader 1205. The pill dispenser 1201 may be removed from the device and brought to a qualified individual, such as a pharmacist or pharmacist assistant, who can provide pills and/or controlled substances for use by the user. Sufficient security is provided, such as using fingerprint security reader 1205 or other device (sensor, voice recognition, etc.) and manual pill dispensing buttons 1204 and the programmable dispensing windows, where ten such programmable dispensing windows are shown in FIG. 12 and programmable dispensing windows 1202a and 12021 are identified. In this arrangement, the user and only the user or an individual identified as responsible for the user can obtain the necessary pills and/or medications. While shown as a pill dispenser, other forms may be taken to dispense bottles, a door that can be opened and closed with sensing provided, and/or other appropriate containment and disbursement hardware. Pill dispensing may entail the device reading a barcode label of the pills being inserted into pill dispenser 1200, and the device may receive and/or provide pill count, dosage, warnings and related indications.

Figure 13:
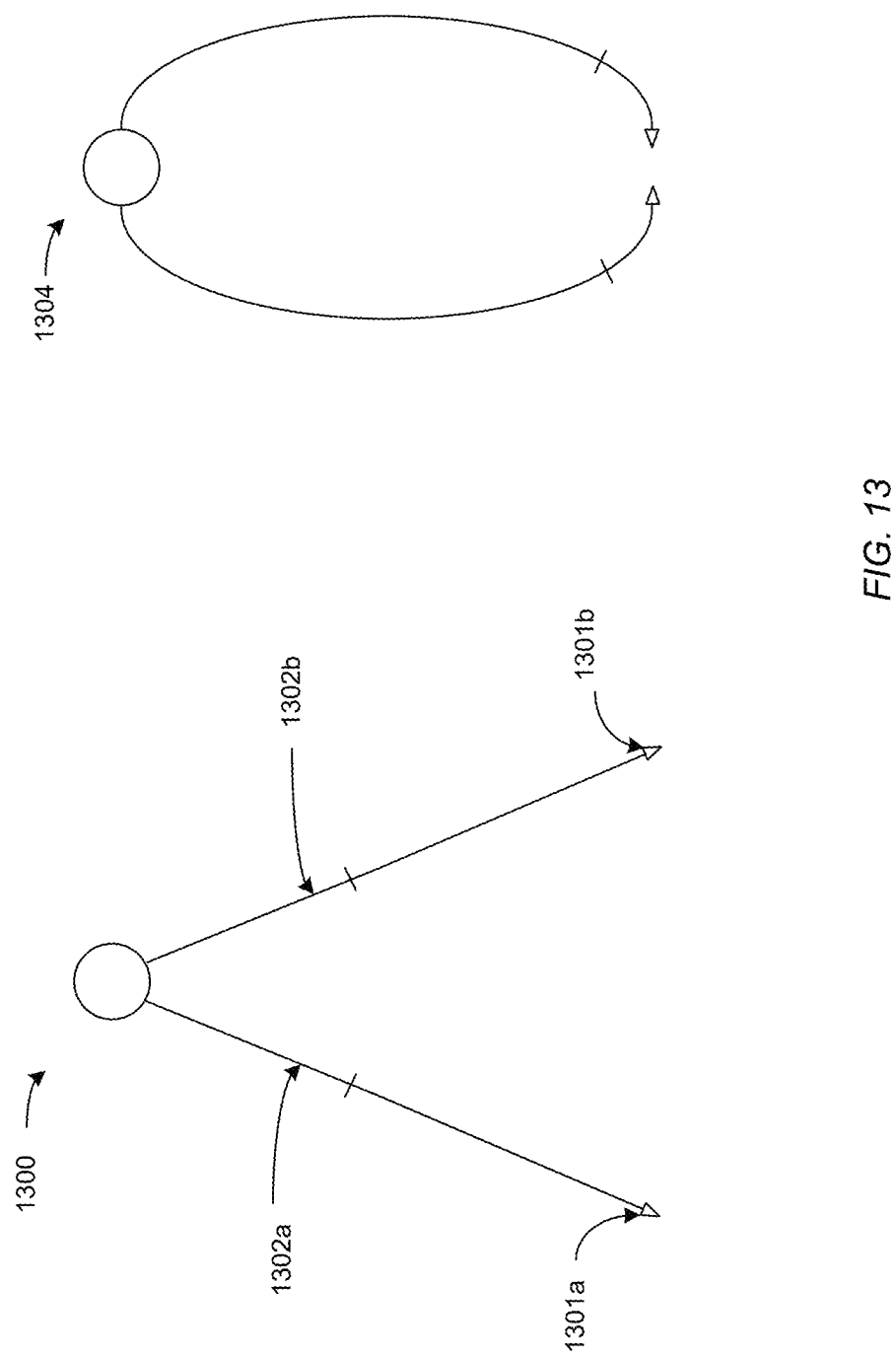
FIG. 13 shows a representative caliper that may be used with the present design.

FIG. 13 illustrates a representative caliper 1300, including reflective tips 1301a and 1301b and telescopic arms 1302a and 1302b meeting at jointed element 1303. An alternative caliper is shown as caliper 1304. Reflective points may be provided.

Figure 14:
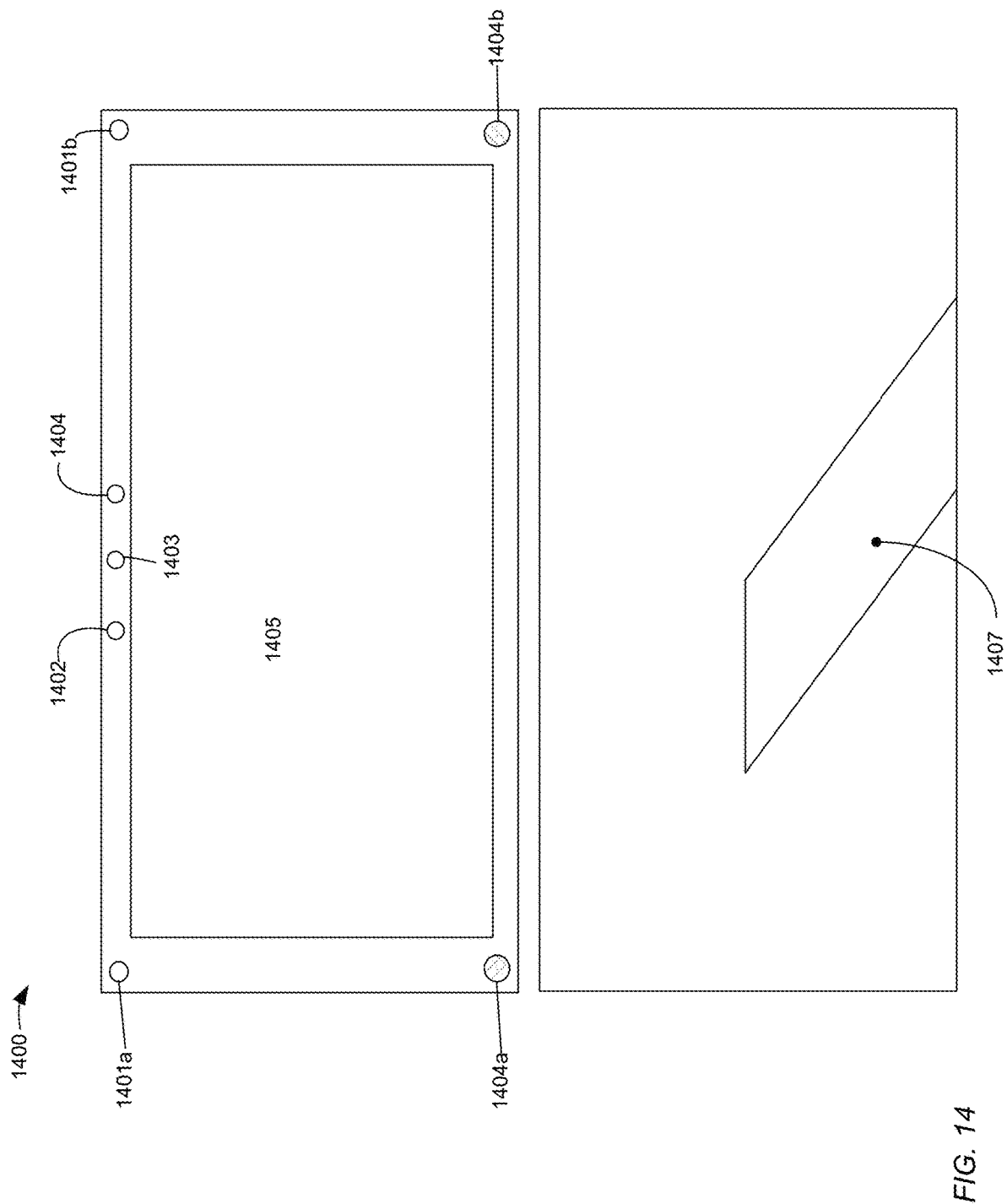
FIG. 14 illustrates a handheld unit that may be used with the present design.

FIG. 14 illustrates a handheld unit 1400. Handheld unit may be carried by the user or other appropriate person for various purposes, including but not limited to collecting data at a remote location, such as a gym, and/or transferring data to a remote location, such as a third party's computing device. Processing functionality is typically offered in the handheld unit 1400, and the handheld unit 1400 typically takes the form of a smartphone or other appropriate handheld device. As shown in FIG. 14, handheld unit 1400 includes a microphone or microphones 1401a and 1401b, a thermal camera 1402, a 3D camera 1403, and a biometric camera 1404, screen 1405 which may or may not be a mirror screen as with the device, and speakers 1406a and 1406b. Screen 1405 may be a touch screen or may be used as a sensor. On the back of the handheld unit 1400 may be provided a stand 1407. A sensor (not shown) similar to the sensor on the device may be provided for authentication purposes (fingerprint, voice, biometric, etc.), or the screen 1405 may be used as a sensor for authentication purposes.

Not shown is the ability of the handheld unit 1400 to connect wirelessly or by wire to either the internet, a cellular service, or other communication service, and the functionality provided may include the ability to collect user data and report the user data to the device and/or obtain user data from the device and/or a remote server or remote arrangement and convey the information to the user or provide the information to a third party. Data may be collected and downloaded at a later time to the device when within range of or communicatively connected to the device, such as device 200. Certain module connectivity may be provided such as via a port or connection.

The handheld unit 1400 may be incorporated into an existing device, such as an automobile part (armrest, headrest, dashboard, console, etc.) or airplane part (armrest, headrest, etc.) or any other type of device. The handheld unit 1400 may be incorporated into devices such as gym bags, purses, clothing (coats, etc.), or even pieces of furniture or other apparatus.

Additionally, but not shown in the foregoing illustrations, a keyboard, either hardware or software, may be provided with the device, such as device 200, or with the handheld unit 1400 such that the user may enter information, request processing, request uploading or downloading of information, and so forth.

Modules provided may include one or more of the following and/or any other combination of devices and/or functionality generally directed to personal care. Modules may include 3D camera-user recognition, recognition of the user using a three dimensional camera or multiple cameras (3D, planar, or holographic), enabling creation of an avatar or virtual avatar of the user, a thermal camera module configured to detect body heat of user, as well as user movements and health related temperatures, a biometric camera module, a scale similar to that shown in FIG. 11 to determine weight, fat, visceral fat, water and muscle content of user, and a heart monitor module configured to determine and provide the heart rate and ECG of the user, track activity of the user as well as changes in heart rate during exercise and/or for the purpose of providing medical alerts. Other modules may include a glucose meter to take blood sugar readings and track blood sugar of the user and may be employed with a medical alert, an oximeter or oximeters that monitors oxygen levels of the user, also possibly used in conjunction with a medical alert, and a blood pressure module that takes blood pressure readings and tracks user blood pressure and may be used with a medical alert. In the present design, connectivity to the device, such as device 200 is provided, and the modules may take any form, such as a small electronic component connected by wire or wirelessly or by any other functional connection to a device, such as in the case of a blood pressure monitor to a blood pressure cuff and inflation device, together with a sensor that senses the blood pressure once the cuff is inflated to the required level.

Medical alert and home alert capabilities may be provided as the device may listen for trigger words as "HELP" or "911." The device may also provide or be connected to a portable panic button.

Functionality and modules provided may also include retinae scanners enabling the identification of the user as well as monitoring eye health and changes, and a finger print reader or readers usable as a security feature and providing temperate reading and other health screening tests.

Modules may take any form, but as an example, they may be the approximate size of a modern car key module and may have a lithium or other appropriate battery in addition to the USB connectivity for both charging and data transmission purposes.

During operation, the present design may employ the video screen of the device and/or the portable unit to display graphical information, alerts, data collected from the modules and/or related devices and may provide information in the form of reminders or even commercials. The device may employ infrared reflectography using 3D laser scanning to create 3D topographical maps of different body parts (face, muscles, breast, feet, hands, teeth, and so forth) using either reflected infrared or lasers of different strengths. Different readings and different algorithms can be employed for different parts of the body, e.g. bumps and lumps on the skin surface, different angles of inclination, joint range of movement, and so forth.

Modules may be manually or automatically updated the user may choose, via the device, combinations of inputs into the modules. The device may provide face recognition capabilities and may be used to recognize third parties (family members, caregivers, pets) and may potentially be employed to sense intruders. The device may take on the attributes and functionality of a computing and/or communication device and may be placed in a sleep mode and awakened through voice activation or other audible communication, e.g. finger snap, clap, or even a button. The device can employ the cameras provided to track eye movement and/or focus on a certain part of the body, and may enlarge the body part or move it through certain ranges of motion. In the fashion area, a user may try on a piece of clothing and the screen of the device may ask the user to turn around and may show the user how the back of the garment appears. In the cosmetics area, cameras may record multiple versions of the same general skin area when the user employs different cosmetics on the area for the purpose of allowing the user to compare and contrast different cosmetics.

The device typically operates using an open platform that integrates data input and reception in conjunction with applications specifically designed for the device. When using the handheld unit 1400, the user may have available a portable accessory to carry one or more modules, such as a glucometer module if eating or a fitness module (measuring heart rate, movement, etc.) if going to the gym.

In operation, user interaction with the device and/or modules may entail the collection of data that may be retained at the device, with data provided from modules to the device via WiFi, Bluetooth, or through a USB connection or by any other means known in the art. The processor at the device may process the data using device formulas and/or applications and may format the data into graphs, charts, diagrams, virtual assistants and other forms to be displayed to the user via, for example, the device (2D, 3D, or holographic) screen. The data and/or information may be controlled by the user and may be sent from the device, such as device 200, to a remote location, i.e. a virtual "cloud," where the information may be collected, analyzed, and/or stored. Once transmitted to the remote devices, the user information may be maintained, analyzed, and specific user recommendations or information may be transmitted back to the user. As currently configured, varying levels of service may be provided. As one example, a gold/silver/bronze level of service may be provided, wherein bronze is simply maintaining data at a remote site, silver is analyzing data and providing recommendations, and gold is a concierge type service where the user may be provided contact with available personnel (physicians, pharmacists, personal shoppers, cosmetics specialists, optometrists, dentists, etc.) and particular needs will be addressed. Different or alternate levels of service may be provided.

As may be appreciated, virtually any type of information may be collected and/or provided using the device/module arrangement provided herein. The ability for the user to indicate specific needs and desires via a keyboard and possibly a mouse, and for the device to display information and act as a mirror enables a virtually unlimited range of functions. A particular user may wish to receive clothing recommendations, and may have her skin tone and hair color determined, and clothing color recommendations provided. Body type may be determined, and age entered, and age appropriate wardrobe selections may be provided based on an analysis provided from the remote location. Another user may have a blood sugar issue, and his blood sugar may be monitored and tracked, and based on his history and desires, recommendations as to what to eat and/or when to eat may be provided to the device and/or to the handheld unit 1400. Another user may want to monitor stock quotes and baseball scores in addition to tracking his progress on a weight loss program. While providing stock quotes and baseball scores is not strictly a personal care function, the present design may offer any type of functionality offered by a computing device and/or tablet and/or smartphone. Thus the user may be exercising with the handheld unit 1400 tracking his progress, i.e. time spent exercising on a treadmill, while the device may display stock quotes or baseball scores. At the end of the user's workout, he may weigh himself using the scale module and may receive meal recommendations and/or a graph of his exercise progress or weight via the device. Thus single or multiple functions and determinations may be provided or made based on functions, applications, and computations available, as well as the needs and desires of the user, in addition to the functionality provided at the remote device arrangement.

Figure 15:
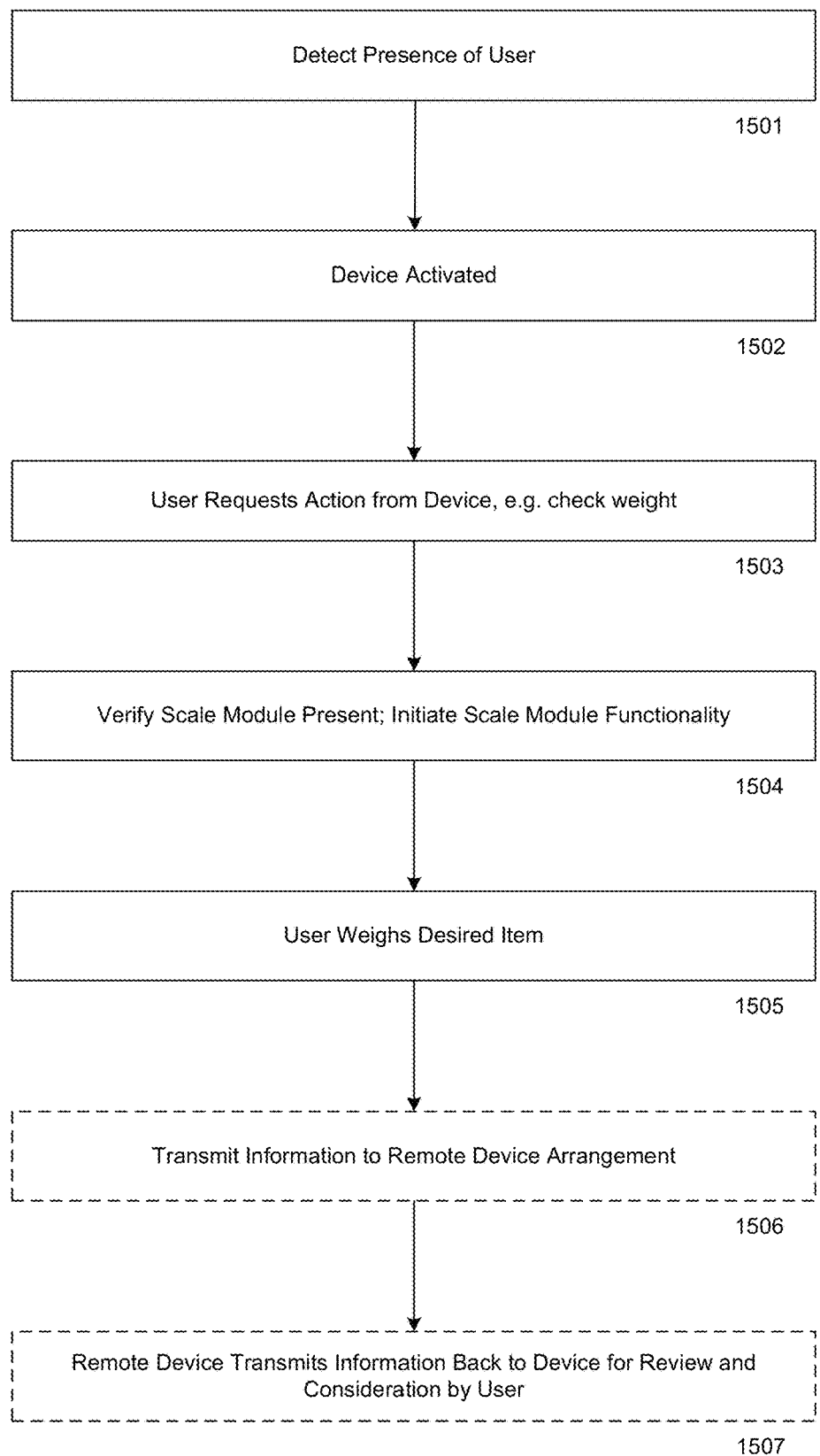
FIG. 15 is a simple functional example/flow diagram of use of a scale module.

A simple functional example of use of a scale module is presented in FIG. 15. From FIG. 15, the device, and more specifically the cameras on the device or the fingerprint reader or other device component, detects presence of the user (e.g. pressing a key on a connected keyboard) at point 1501. At point 1502, the device, such as device 200, is activated and may come out of a sleep or hibernation state as appropriate. At point 1503, the user may ask for an action from the device, in this case checking the weight of a desired item using a scale. The device determines whether the appropriate module is connected or available, here the portable scale module. If not, the device prompts the user to connect the module to the device, and the scale module functionality is initiated as shown in point 1504. Weight information may be provided on the screen of the device, and specific information may be provided—commercials, recommendations, graphs of weight readings over time, most recent weight, and/or other information.

At point 1505, the user weighs the desired item, and the resultant weight is provided to the device, and more specifically the processor in the device. The screen of the device may display current weight and tracked weight, either graphically or numerically. At point 1506, which is optional, the device, such as device 200, may transmit the information to a remote device arrangement for further processing, such as determining recommendations for a man the user's age and in the user's situation. At point 1507, the remote device arrangement may send user specific information back to the device, such as device 200, for review and consideration by the user. Emails, text messages, phone messages, and/or other user selected communication methods may be employed to inform the user of determinations made at the remote device arrangement. Certain information may be provided from the remote device arrangement to the device to enhance operation, such as locally storing recommendations for the particular user determined at the remote device arrangement. The device may at that point return to a hibernate or sleep mode or may continue operation as desired.

Functions may vary and may depend on what is required, and as may be appreciated, any list of functions may be changed, improved, reduced, or otherwise altered depending on a variety of factors, including but not limited to popularity of the functions, needs and desires expressed by users, use patterns, costs associated with apps and functions, and so forth. Certain functions may be provided either locally, i.e. at the device, or remotely, i.e. at the remote device arrangement, or a combination of both. In general, the system, including the device and remote device arrangement, receive information and queries and respond appropriately for personal care issues that arise.

Examples of the determinations made and functions provided are as follows. In the area of health, lung health may be maintained and monitored, and the device may determine respiratory rate (RR), $CO_2$ level, lung volume, pulse oximetry, breathing characteristics, jugular vein distension (JVD), pitting edema, and/or body pH level. The device may respond with a chart including a degree of hypoxia, a graph with the user's lung volume as compared to users of similar age and sex, and a pitting edema score. In the area of heart health, the device may collect pulse/heart rate, blood pressure, heart rhythm, and EKG values with appropriate modules. The device may determine and/or report a graph, raw data, and or percentile data, as well as recommendations. In the area of nose and sinus health, the system, including the device, handheld unit, appropriate modules, and/or remote device arrangement, may analyze the nose for deviations in shape and/or color, flaring, discharge, and nasal patency. The system may then provide raw data, a digital model of the nose and/or sinus, and provide a percentile, score, and/or chart. In the field of eye health, the system may assess or determine sclera color, visual acuity, peripheral vision, analyze the pupil, iris, sclera, and so forth, determine eye pressure, redness or dryness, and eyelash evenness, and the system may provide a digital model of the eye, a scoring of quantities such as peripheral vision, raw data, percentile values, a chart, and a chart or graph.

Many, if not all, of the health related evaluations may result in a combination of a score or scores, raw data, percentile, and a chart or graph of the health of the particular site. It is to be understood that these and other relevant information (recommendations, warnings, pictures, etc.) may be determined and provided as appropriate, but that all such determinations may be made and provided when assessing health parameters.

In the area of ear health, the system, again including the device, handheld unit, appropriate modules, and/or remote device arrangement, may assess the internal ear, including the external, middle, and/or inner ear, analyze the external ear (auricle and pinna), determine degree of hearing loss, and perform a bone conduction evaluation (Weber/Rinne) Dental or oral care health may include an assessment of lips, inner and buccal mucosa, tongue, mouth floor, teeth and gums, hard and soft palate, salivary glands, and tonsils. Many of the assessments discussed may be made using a camera or recording device, but others may require modules specially made for the task. Digestive health may be assessed using food intake, stool analysis, BMI (body mass index), and weight. Liver health may be assessed using skin color, sclera color, ammonia levels in urine, level of consciousness, abdominal distension, weight, total body water, skin irritation, activity level, and/or stool color. General hormone balance may be assessed according to a hormonal profile, activity level, weight gain, EKG, heart rate, mood, level of anxiety, headaches, and/or sleep pattern. Kidney health may be assessed according to daily urine output, blood pressure, glucose level, and/or degree of edema. Muscle health may be assessed according to strength, tone, size, symmetry, fasciculations, tremors, arm/leg circumference, and activity tolerance.

In the present design, the user may be monitored using a module or the user may be queried directly or may offer the information requested. For example, the user may be queried as to "have you experienced any muscular tremors in the last week" and she may respond "no." Alternately, the user may be asked "what has been your activity level in the last day?" and may provide the user with options (none, mild, moderate, extensive, or quantities, such as ran for 20 minutes). Various options regarding obtaining the necessary information, including the necessary health information, may be provided. The user does not need to provide the information—the information may be provided by a third party (caregiver, spouse, etc.)

Nail health may also be assessed, analyzing convex curvature, i.e. the angle between the nail and the nail bed, and in addition to the other reports and/or information provided to the user, he may receive a graph of a degree of clubbing (normal, early, or late), based on nail bed shape and angle. Testicular health may be assessed according to a pain scale, new lumps, heaviness in scrotum region, and/or testicular swelling. Obstetric health may be assessed—weight, heart rate, blood pressure, portable ultrasound results, fetal heart rate assessment and analysis, and food intake, for example. Bone health may be assessed according to bone density, calcium level, activity level, pain scale, swelling, nutritional intake, and a bone densitometer score. Mental health may be determined by assessing speech recognition, level of consciousness (LOC), weakness on one side, blood pressure, visual changes, and/or NIH score. Ovulation health may be assessed by determining a surge in Luteinizing Hormone (LH) urine, analyzing cervical mucus consistency and/or basal body temperature (BBT). In addition to the other health information provided (raw data, graphs, charts, etc., ovulation results may include a digital calendar or listing of best ovulation times.

Spine health may be assessed according to structures or deformities, warmth, swelling, range of motion (ROM), presence of scoliosis, and gait. Joint health may be assessed by evaluating warmth to the area, ROM, swelling, presence of nodules, and/or gait. Skin health may be assessed according to skin turgor, color, skin breakdown, and degree of edema. Hair health may be assessed according to hair distribution, hair density, color, moisture content, dryness, texture, and presence of infection and/or infestation. Breast health may be determined based on swelling around the breast and armpit, pain level, changes to nipple, discharge, signs of lumps, and/or menstrual cycle issues. Information provided relative to breast health may additionally include a video showing a proper breast exam, and a digital model of the breast of the user or a hypothetical breast, again for examination purposes.

Foot health may be determined by collecting signs of infection, color, hair distribution, skin integrity, and degree of pitting or edema. In addition to the other reporting data, the system may provide a digital model of feet or the lower extremities. A general collection of parameters for the user may occur, including but not limited to collecting heart rate (HR), temperature (T), basal body temperature (BBT), respiratory rate (RR), SaO2, pulse oximetry, CO2, systolic blood pressure (SBP), diastolic blood pressure (DBP), urine chemistry, dry blood work, joint ROM, spine flexibility, muscle strength, BMI, total body water (as a percentage of body weight) in relation to age and sex, electrocardiogram (EKG), lung capacity (TV, TLC, VC, FRC, RV), height and weight, and body pH level. These and other pertinent values may be collected and reported and/or continuously tracked.

In the area of fitness and wellness, different module specific interactions may occur where data is received by the system (device, handheld unit, remote device arrangement, module(s)) and certain information assessed and provided. In the area of fitness, the system may collect or receive user goals, weight loss values (current or desired), general fitness, preparation for an athletic event, muscle building, and rehabilitation from injury. Output may include an individualized fitness program as well as graphs and charts and recommendations. In the area of body building, height, weight, neck, chest, upper arm, waist, hips, and any other relevant area may be measured, and information about body fat provided as well as changes in body measurements. For sweat, the device may be provided with a module that analyzes user sweat and provides information on total free amino acids, ammonia, protein concentrations, and nitrogen balance of the user, detects a negative nitrogen balance, gives dietary recommendations, recommends post workout recovery meals, and recommends a dietary and supplement plan. For workout performance, the system, and possibly a module in the system, analyzes body mechanics during exercise by measuring weight distribution, relative angles at joints during exercise or body heat via thermal infrared camera. The device provides corrective user feedback on proper body mechanics during exercise. In the area of nutrition, the user may input daily food intake via picture, barcode scanner, or may select items consumed from a pull-down menu. Also provided or calculated are total calories, protein, carbohydrates, fat, and fiber. The system may recommend dietary changes toward fitness goals and may provide charts and graphs.

In the area of exercise, the system may collect or receive user submitted photos of gym equipment (at home or in gym), may enable interaction with an A1 Personal Trainer, where the user communicates in real time with the A1 Personal Trainer, time between sets, number of reps and weight lifted, body posture via angle of shoulders to waist and feet, and the system may recognize available equipment and build an exercise program. A trainer may observe the user while completing exercises and give real time feedback about technique. The system may provide motivational instruction. Recommendations by the A1 Personal Trainer may optimize user exercise output. Physical health at work may be assessed by calculating angle of the body while seated and doing work, assuming the device or handheld unit is available at a representative workplace. The system may also calculate height of desk, chair, keyboard, and mouse. The system may recommend corrective body posture and ergonomic corrections to the work station. Physical health in the case of injury may be assessed, wherein a provider or the user or other appropriate individual may input the user's injury or injuries. The device may then create an exercise regimen based on the user's needs and specific injury.

In the wellness area of sleep architecture, the system may measure room temperature, amount of room light, noise, track user sleep/wake cycle, and the amount of movement during sleep. The system may recommend changes to sleep architecture. Tracks changes and saves users optimum sleep requirements. The system may also address menses, determining date of first day of the menstrual cycle, length of bleeding, bleeding volume, daily temperature, and may provide recommended dietary changes.

With respect to fashion, the system may assess body shape measurements, i.e. biometric points, body shape, and may measure four separate points—shoulders and hips, in the form of an "X." The system, including but not limited to the remote device arrangement, may provide recommendations on clothing style and cut, perform "body blocking," and provide a "virtual 3D mannequin" of the user based on calculations. The user may be allowed to "try on" various styles/cuts/colors of clothing on the virtual mannequin. Based on mannequin sizes, retailers will have better information on the user's particular clothing needs and wants. The system may also assess secondary body measurements, determining height, weight, BMI, arm length, arm circumference, thigh circumference, torso length (long, short, average), breast size, shoe size/width. From these secondary body measurements, the system may determine detailed body composition, make specific suggestions as to clothing, styles, and accessories through the device and available from retailers, and creation of a "virtual mannequin" can increase details known about the user's body image to both the user and a retailer. The system may also determine body size changes, assessing mirror and major changes in weight and body changes due to pregnancy, and providing revisions or potential revisions to style, size, color, and cut of clothing, as well as suggestions.

The system may also assess user demographic information, such as age, race, geographic location, profession, income, education, marital status, and number of children. From this, the system can determine a presentation specifically tailored to the user, determine style suggestions, price points, and clothing styles relating to seasons, temperatures, and precipitation, and allows retailers to focus on a specific consumer profile. The system may additionally determine clothing wear, possibly employing a sensor in user clothing, to determine date of wear, number of wearings, and frequency of wearings.

With respect to cosmetics, the system may assess tone and pigmentation by determining skin undertone based on the color of the major vein around the wrist and by blue, yellow, red content against a white background. Results determined may include a 3D graph, a personal color wheel for hair, a personal color wheel for make-up, prescription skin care recommendations, over-the-counter skin care recommendations, peel recommendation, laser resurfacing options, and continuous updates and recommendations. Skin category may be assessed, including determining consumer inputs, oil content of skin, and reflexive skin properties, and providing a graph of skin, oily to dry, recommended moisturizing and cleansing creams. The system may also evaluate pores, determining distribution and spread measured by number per square centimeter and measure color and size of pores. From this information, the system may provide information including a graph, chart, updates and recommendations, microdermabrasion, chemical peels, facial cleansers, and creams.

Acne may be assessed according to distribution and spread measured by number per square centimeter, measurement of color and size of pores, acne location via a topographical map of the user's face, depth and height, and cystic versus black head. Information provided and reported may include a graph, chart, topography, updates and recommendations, microdermabrasion, chemical peels, facial cleansers, creams, laser resurfacing, and information regarding or from a dermatologist. Scars may be assessed based on discoloration, size, location, depth, and height. Again, based on this, the system may recommend or provide a graph, chart, topography, updates and recommendations, microdermabrasion, chemical peels, facial cleansers, creams, laser resurfacing, and information regarding or from a dermatologist. Skin elasticity may be assessed based on skin turgor, muscle and skin laxity, and nasolabial fold measurement. The user may be provided with a graph, topography, charts, updates and recommendations related to skin elasticity, firming products, and/or laser tightening methods.

Wrinkles may be assessed based on measurements of crow's feet around the eye, length, depth and quantity of wrinkles in particular regions, frown lines, forehead wrinkles, wrinkles around the mouth, wherein all wrinkles may be assessed based on wrinkles per square inch. The system may determine and provide a graph, chart, topography, updates and recommendations, cosmetic grade skin care, medical grade skin care, Botox treatments, fillers, chemical peels, and/or specialized laser procedures. As may be appreciated, more severe skin issues may call for added recommendations, procedures, products, and/or treatments.

Facial hair may also be addressed by determining follicles per square inch, coarseness, length, diameter, color, and/or location, and the system may provide graphs, charts, updates, and recommendations relating to waxing, medicated creams, and laser hair removal. Facial attributes may be assessed and recommendations or information provided. Facial attributes evaluated include shape, position of eyebrows relative to eyes, distance from medial eyebrow to medial canthus, distance from lateral eyebrow to lateral canthus, distance of lateral canthus to medial canthus, spread and distribution of hair per square millimeter, length and diameter of hair, shape and contour of eyes, diameter of iris, distance measurements of eyebrows, ridge of nose, and forehead/hairline, width of eyelids, distance of the upper eyelid from the lower lid at multiple locations, eye color-measure by the three basic color red, blue, yellow, color and discolorations of sclera, eyelashes measured by follicles per square millimeter, coarseness measured by the length, and diameter of each hair, with information provided including graphs, charts, topography, updates, and recommendations regarding shaping, make up, medications, Botox, and even surgery.

Facial symmetry of hair may be assessed, determining length of forehead and measurement of trichion to glabella. The system may recommend facial hair profiles and may provide graphs, charts, and updates. General face shape may be assessed, including measurements of trichion to menton, ear lobe to ear lobe, trichion to glabella, trichion to arch of eyebrows, infratip of nose to menton, menton to mandible, mandible to pre auricular points, and/or length of filtrum. Results provided may include graphs, charts, topography (as used herein, topography includes maps and or data related to topography of the particular feature(s) or region), updates, and recommendations including hair, make up, and jewelry.

Measurements and determinations of particular features may be made, including but not limited to nose, lips, cheeks, jaw lines, chin, and neck, with assessments made using cameras and any other appropriate devices or modules. Graphs, charts, topographies, and updates may be provided as well as feature specific recommendations, such as makeup, surgical procedures, makeup, fillers, moisturizers, treatments (e.g. Botox), and so forth.

Teeth may also be assessed based on measurement of teeth size, separation distance of teeth, angle of teeth, color or shade, and/or color of gums (measured by red, blue, and yellow against white). In this cosmetics area, other outside factors may be assessed—current medications and/or current diagnoses, for example. The system may make specialized recommendations pertaining to skin health with these medications and diagnoses, and may make recommendations of supplements and/or foods to maintain skin health.

Certain personality factors may be determined, such as desired look during the day or night, age, gender, geographical location, income, and/or occupation. From this, the system may determine graphs and charts, and may make recommendations such as color pallets and application instructions.

In the area of pharmaceuticals, the present system may make additional assessments and may determine recommendations and provide information to assist the user in his or her personal care. One area is prescription medications, wherein the system collects user name, quantity, dose, administration, duration of usage, refills, adverse reactions, use in specific populations, over dosage symptoms, over dosage signs, prescriber name, prescriber address, prescriber phone number, pharmacy name, pharmacy address, pharmacy phone number, controlled substance schedule (if applicable), price per unit, and medication expiration date. Certain information may be collected from third party sources if available, as is the case with other functions performed by the system. For example, if the medication is known, the system may submit a query seeking adverse reactions, or if a pharmacist is known, the system may seek the address and telephone number of the pharmacy from an online source. As may be appreciated, such specialized functionality must be provided in the system, i.e. seeking information from a particular site, seeking the specific information needed, and obtaining the information. The device may perform this functionality, or such functionality may be performed by the remote device arrangement or a person associated with the remote device arrangement.

Information provided by the system may include a drug interactions alert, a refill alert, alternative medications options, generic medication options, an electronic update of current medication list to the device cloud, filling of the pill dispenser, lock filling into medication drawers if applicable, providing alternative price per unit information from other suppliers, an expiration date alert, and a next dose alert through cloud based system.

Over the counter supplements and supplies may also be assessed and information provided. Assessments may include name, quantity, dose, administration, duration of usage, refills, adverse reactions, use in specific populations, over dosage symptoms, over dosage signs, prescriber name, prescriber address, prescriber phone number, store name, store address, store phone number, price per unit, and/or expiration date. The information provided to the user may include a supplement interactions alert, a refill alert, alternative supplement options, an electronic update of current medication list, filling of a dispenser, alternative price per unit from other suppliers, and/or coupon options from suppliers.

Health markers may also be assessed. Information assessed may include Indication(s) for particular drugs (allergies, etc.), heart rate, temperature, respiratory rate, pulse oximetry, systolic blood pressure, diastolic blood pressure, urine analysis, blood analysis, breath analysis, weight, body pH level, sclera color, pupil size, lip color analysis, skin color analysis, mini mental status exam, pain scale, electrocardiogram, and/or BMI. The system may take these inputs and make relevant determinations including a score, raw data, percentile, chart or graph, measurement of physical or mental response to a medication or supplement, possible medication or supplement overdose symptoms alert, and possible medication or supplement overdose signs alert.

Dispensing of prescriptions may be assessed and information provided. Assessments may include name, quantity, dose, administration, duration of usage, and refills. The system may provide a visual display of one or more of the following: substance name, substance remaining quantity, substance dosage, route of administration, allowed refills, and/or substance expiration date.

The present design may be used in various scenarios, including but not limited to use of the design for pets or animals as well as plants in addition to human personal care. In the pet scenario, the device may monitor a pet, such as a body temperature of a pet, using a module, and/or the location of a pet, such as using a collar with a GPS component or other position determining device. In the horticulture arrangement, for example, plant health may be monitored and plant care provided as appropriate. In one instance, a device may measure amount of water available to a tree, and if deficient, may notify a person or service to provide water to the plant, or may cause a sprinkler or watering apparatus to turn on automatically.

Interactive Diary

The present design further includes an interactive diary function wherein the user can keep track of information and data related to his or her personal care and such information can be employed to better provide personal care for the user, either from an off site location/central server device or arrangement or from the device itself. The interactive diary tracks pertinent parameters to the individual user in the area of personal care and wellness and may offer at least one recommendation. Interactive diaries for personal health and wellness may be offered in but not limited to the areas of health, fitness and sports, fashion, cosmetics, education, travel, finance, nutrition, pharmaceuticals, pets and/or horticulture. For example, the current design may monitor blood pressure and may track blood pressure. However, blood pressure is merely one data point in a plurality of data points related to an individual user, and when blood pressure is considered in connection with factors such as blood pressure readings over time, family history, weight, salt intake over time, smoking history, coffee intake over time, level of exercise, a more complete representation of the person may be determined. In such a situation, the individual may be encouraged to reduce coffee intake and/or exercise in a manner conducive to her ability. For example, if she has back issues, this may be known and encouragement to swim a certain amount per day three days per week might be recommended. A different person with a different profile but an identical blood pressure reading may be encouraged to decrease salt intake, reduce smoking, and to increase exercise by running two miles instead of 1.5 miles every day. The interactive diary function encourages the user to provide more information and obtains a more complete profile of the individual. In another example, the user may seek to purchase a new shirt; certain options may be offered to him, such as collar style, buttons, cut, sleeve length, etc., and the program may recognize prior preferences using the interactive diary and offer certain options to the user based on past history or indicated learned preferences.

A further example is in the area of sports where an interactive diary for a child playing any sport can be functionally tailored to act as an interactive diary used by a professional athlete. The interactive diary may, as one example, collect and track sizes and functionality of certain muscles and ligaments, nutritional requirements and goals, track progression of skill sets desired, as well as vital signs affected by each workout. Also, the desired and available fashions for that sport as well as skilled coaching recommendations tailored to that specific athlete, whether a child or a professional athlete sharing the same sport tenure, may be assessed and recommendations provided as desired.

The interactive diary consists of collecting information at the device in accordance with the foregoing design, including collecting information using the modules provided that are interchangeable and as a result specific to the user. The information collected may be passed to the central server arrangement or an offsite location and may be stored and/or processed offsite. Alternately, the device may store and process the information, or both local and remote devices may offer part or all of certain interactive diary functions.

Figure 16:
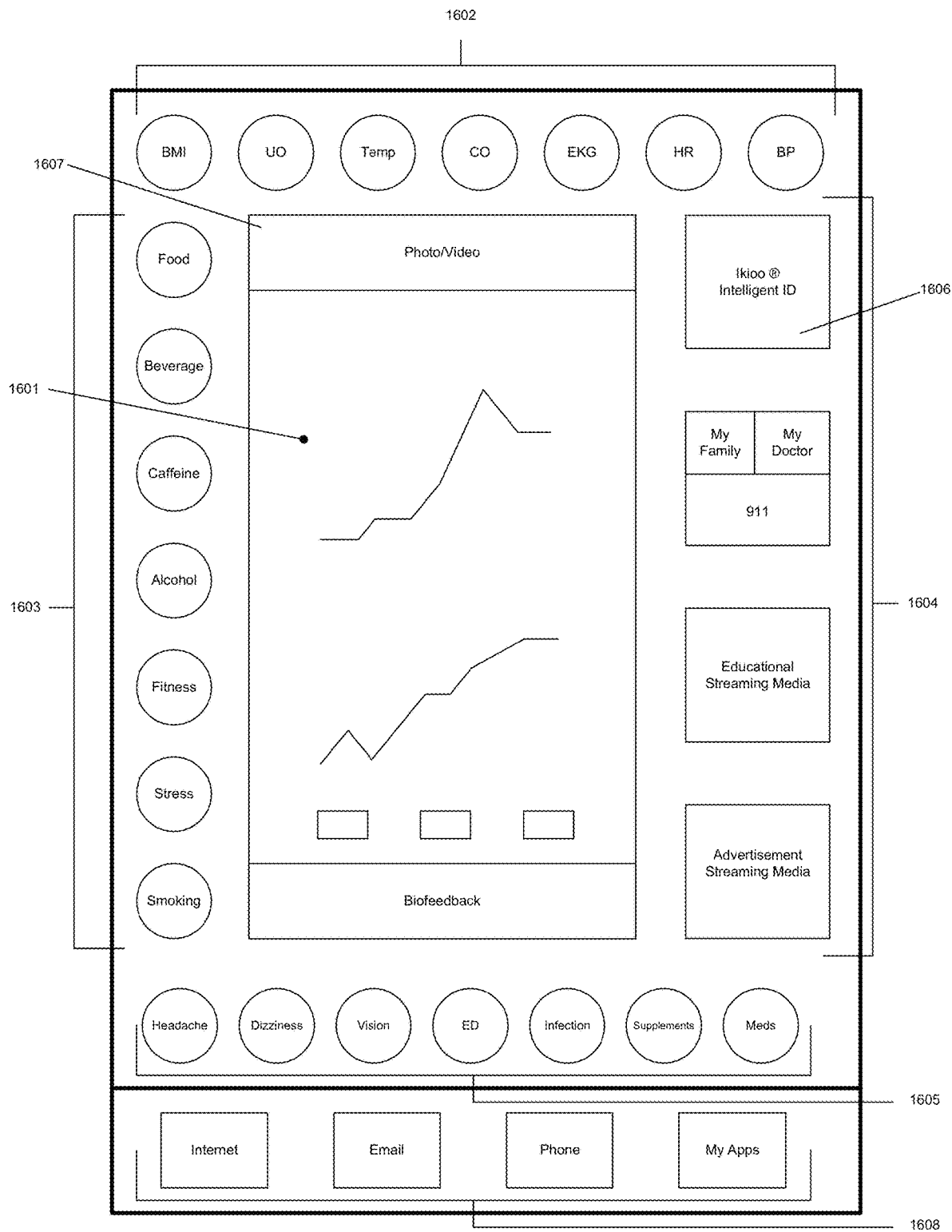
FIG. 16 illustrates an appearance of a screen operating in accordance with the interactive diary function.

FIG. 16 illustrates an appearance of a screen operating in accordance with the interactive diary function, and this may be offered on the personal care device discussed above or other appropriate hardware. From FIG. 16, there is provided a central region 1601 and various peripheral regions including upper region 1602, left region 1603, right region 1604, and lower region 1605. A single control button 1606 causes a return to a central or top screen when pushed irrespective of the active screen.

Central region 1601 may include traces of information being measured, i.e. the biofeedback being measured using a module or modules and the mirror device. The buttons presented in FIG. 16 may either be hard, physical buttons or may be soft buttons activated by user touch. Buttons in the top row generally correspond to readings taken of the user's health, including but not limited to blood pressure, heart rate, EKG, cardiac output, body temperature, urine output, and BMI (body mass index). In one embodiment, pushing the button once results in the system showing a tracing of the parameter in the central screen. Pushing twice maximizes the central screen to cover the entire screen, and pushing the button for a predetermined amount of time, such as three seconds, the central screen is maximized and user editing is enabled, such as editing of urine output, etc., using a keyboard, voice, or in some other manner in accordance with the device and system described above.

Left region 1603 includes certain activities that are or may be relevant to the individual user, including but not limited to food consumed, beverage consumed, caffeine consumed, alcohol consumed, fitness and exercise accomplished, stress factors, and smoking. The user may enter what he or she consumed or did, and this may be tracked or attributes displayed. The lower region 1605 may include various symptoms and/or prescriptions taken, including but not limited to choices such as headache, dizziness, vision issues, ED (erectile dysfunction), infection, cramps, and supplements, vitamins, medicines, etc. In this embodiment, a single push of the associated button may provide a time and date stamp and propagates the selection to desired locations, local and remote. Two pushes maximizes the screen and a three second button push in one embodiment allows editing of the entry, such as supplement taken, type of vision issue, duration and severity of headache, and so forth.

A lowest region 1608 includes other relevant functionality, and may include selections for internet, email, phone, or desired applications or clusters of applications. Different functions may be provided, and selecting these buttons takes the user to the selected option.

A photo/video button 1607 may also be provided. Pushing beverage and pushing photo/video button 1607 causes a photo or video file to be created or identified and the photo or video can be provided to a beverage file storage device or area. In various instances, selection of one of the buttons in left region 1603 provides an associated screen for entry of further information, e.g. quantity of beverage consumed, type of medication taken, headache severity, etc. Selection of the parameters offered, or entry of data according to the parameters offered may be stored and processed locally and/or remotely.

Right region 1604 in the embodiment shown includes four functions. The top button is an intelligent ID (Interactive Diary) button 1606 that returns to a top level for all screens except the main screen. The second button is favorite contacts, and may include name, phone number(s), email address, and may include emergency numbers. A limited number of contacts may be provided, or if desired, as many as requested, or all. Selecting one of the contacts may put the user in touch with that contact. The bottom two elements may be streaming media and advertising if desired by the user and/or a provider, such as a service provider.

The central window, or central region 1601, shows a corresponding page when one of the peripheral buttons is selected. Buttons may change to accommodate enhanced functionality. The corresponding page may be a home page, a selected page, an image, or other appropriate page. The device camera may be activated by selecting "photo/video" on the central region 1601. Selection of "biofeedback" when the user is being monitored provides the monitored results to the user, such as a graph, with other factors provided as appropriate, such as consumption of foods, beverages, smoking, etc. when monitoring blood pressure, temperature, etc. Positive factors may be provided in one color while negative factors may be provided in a different color. Selecting a button twice, such as the biofeedback button, may maximize the biofeedback screen. Selecting the button for a particular amount of time allows the user to edit parameters.

The system may also provide recommendations. Recommendations may be dynamically updated and may include recommendations on food, diet, supplements, hydration, fitness and exercise, biofeedback recommendations including options such as meditation, medication recommendations, including when to monitor intake, sodium intake, alcohol intake, caffeine intake, smoking, and stress avoidance recommendations.

Figure 17:
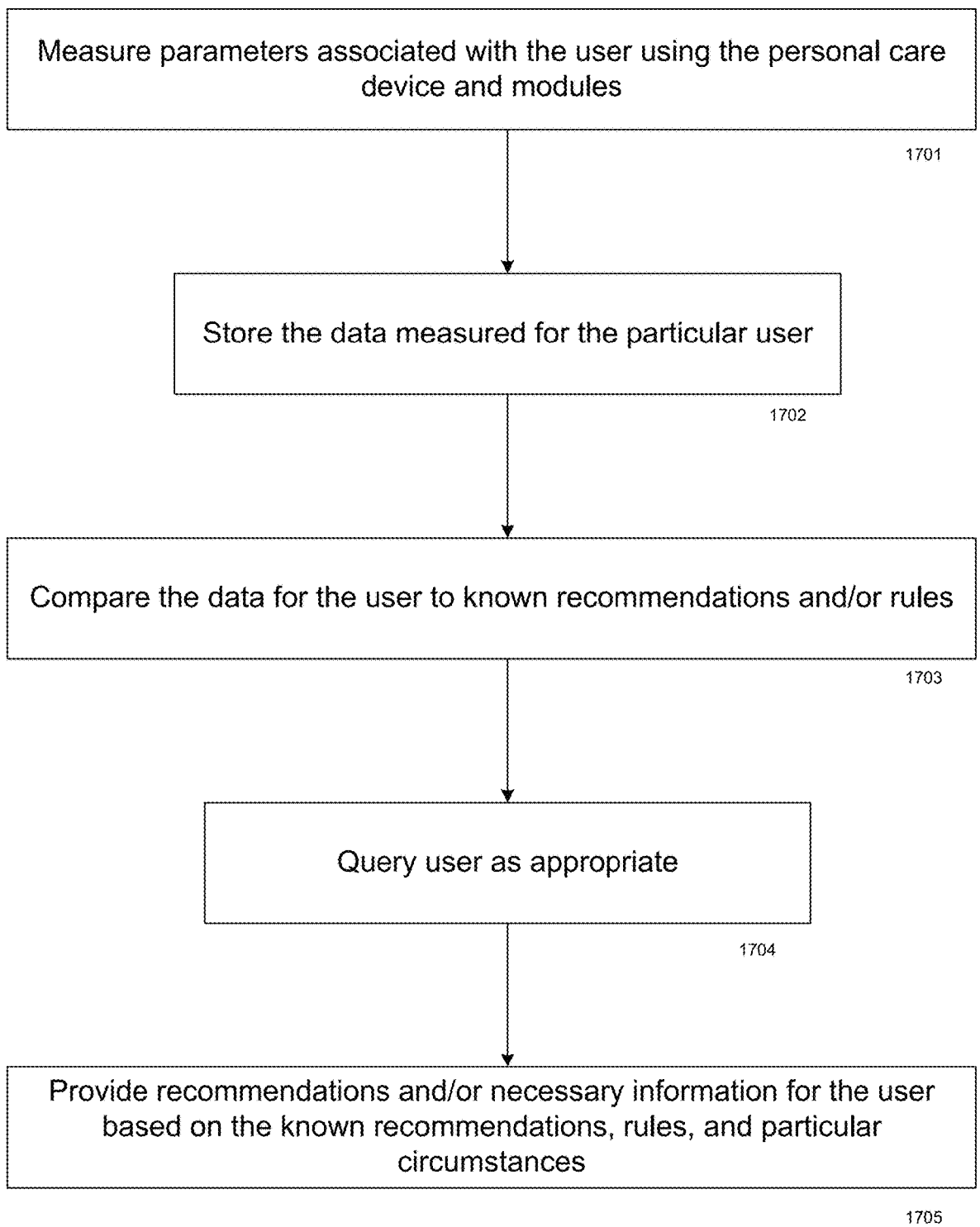
FIG. 17 shows one embodiment of general operation of the interactive diary function.

The system may operate according to the representation of FIG. 17 with respect to the interactive diary. From FIG. 17, the device initially measures parameters associated with the user using the device described herein and the various modules applicable to the particular user. As an example, the user may measure her temperature over a series of sessions, or even over a single session. The data measured is stored at point 1702 for the particular user. At point 1703, which may be user initiated, system initiated, periodic, or otherwise instantiated, the system takes available information as appropriate and compares this information with known recommendations and/or rules and may optionally query the user at point 1704 and provides recommendations and/or necessary information for the user in point 1705. As an example of the querying at point 1704, if the patient is a young man who has seen a rise in his temperature, such a rise in temperature may be unexpected but the user may be provided with questions or recommendations such as "are you feeling ill?" "do you have a headache?" "do you have a normal appetite?" and so forth in an effort to identify the problem. The user may be presented with information at point 1705 such as "Jeff, you have an elevated temperature. You should drink fluids over the next 24 hours, and it is recommended you drink six glasses of water in the next day. Please take your temperature again in approximately four hours" or something similar.

While health has been the focus in many of the examples provided, other personal care functions may be similarly offered and buttons provided or added that provide functionality in the other personal care fields. By way of example and not limitation, clothing preferences may be selected or input or provided by a user, such as I purchased shirt X and like this shirt very much—I like the color and fit, but I do not like the collar (too narrow) and color and style of the buttons. This information can be provided by the user at point 1701 and stored at point 1702. At point 1703, the system takes available information as appropriate, such as the jacket being considered, and compares this information with known recommendations and/or rules in point 1704, e.g. clothing preferences, likes, dislikes, etc., and provides provide recommendations and/or necessary information for the user in point 1705, such as "this jacket should work for you in size and style but may be too large in the shoulders."

Various menus may be provided to guide the user through what he or she has done or encountered. For example, in the food realm, the user may be guided through screens such as dairy, meat/protein, grains, salads, vegetables, fruit, junk food, miscellaneous, etc., Beyond this, for example, if dairy is selected, the user may be directed to yogurt/cottage cheese, milk, cheese, ice cream, etc., and once selected, the user may specify the quantity consumed, e.g. number of ounces or fluid ounces. There may be overlap between menus, such as if a "non-alcoholic beverage" is selected, choices such as water, soft drinks, sports beverage, juice drink, milk, etc. may be provided.

As an alternate, the user may enter a choice, purchase, or relevant information manually, e.g. typing in "6 ounces of kombucha" when kombucha is not offered as a selection. Such an entry may be considered by the system, including but not limited to by a human, the manually entered information classified or categorized, and the system may propagate changes to individual or all devices deployed in the field. For example, the kombucha entry may be determined to be a drink having certain benefits, and may be categorized or considered in relation to the person's digestive and/or overall health, and a kombucha option may be provided for the user, a group of users, or all users and considered in the future.

In the exercise realm, the user may be presented with a question as to the type of activity performed and duration of the activity in some measurable quantity (miles run, time spent, stairs run, etc.) Examples of activities may include but are not limited to walking, running, playing basketball, baseball, hockey, fencing, golf, as well as activities such as gardening, backpacking, mowing lawns, shoveling snow, skipping rope, stair climbing, rowing, weight training, housework, dancing, etc. If desired, such activities and quantities may be converted into a measurement such as calories (believed) expended, based on attributes such as activity, time spent, weight of the user, etc.

Stress values may also be measured, such as the user identifying a particular category or classification of stress, e.g. work, home financial, children, parents, other, as may smoking, e.g. cigarettes, cigars, pipes, vaporizers, hookahs, marijuana, and so forth.

Issues such as headaches can be broken into components for selection/reporting by the user, such as location (front, right side, left side, top, back), intensity (e.g. scale of 1 to 10) and type (dull, sharp, throbbing, numb, gripping, migraine, "worst ever," etc.) Dizziness may be quantified, such as by vertigo, standing dizziness, lying down dizziness, or otherwise. Vision issues can be quantified, for example, as blurry vision, tunnel vision, floaters, flashing light, loss of vision, or red eye. Infections, ED, and other afflictions may also be quantified or categorized as appropriate.

As may be appreciated from the foregoing including the depiction in FIG. 17, the system may provide recommendations, diagnoses, ask for additional information, or simply collect data without providing any feedback, where all of the foregoing is selected by the user and/or a central server. If someone does not want to receive comment or recommendation, such as for a purchase of a particular cosmetic, he or she can disable this or simply not look at or give any weight to a recommendation or suggestion or diagnosis.

With respect to blood pressure, for example, systolic and diastolic blood pressure may be combined into a blood pressure or "BP" function offered on the top page. Selection of the button may cause a transition to a health page or screen. The system may employ blood pressure cuffs or other appropriate devices used together with an appropriate module to assess blood pressure of the user (SBP, DBP and heart rate may be measured). A time stamp and/or GPS location may be provided. Other screens and other functions may be provided in a similar manner (BMI, etc.)

Thus the current system measures parameters relating to the individual and collects these parameters, either locally or remotely or both, then assesses the parameters, again either locally, remotely, or both, to make a determination about the user and/or a recommendation relating to health, fashion, cosmetics, etc. For example, if the user is interested in purchasing a particular skin cosmetic, she may provide the information of the cosmetic (brand, type, product number, SKU number, or other identifier) and the system may search previously purchased cosmetics, as well as preferences for or issues with previously identified cosmetics, and may indicate such a cosmetic recommendation, such as "not preferred" or "too dark based on previous liked purchases" or "product X is what you should purchase based on past expressed preferences." The user may be periodically prompted to update preferences. For example, fashions may change, and what the user liked last year may be disliked this year, and he may be consulted about past indicated preferences, particularly when a contrary preference is provided. For example, if a man is interested in purchasing a pair of loafers but had previously only expressed an interest in tie shoes, he may be queried if he prefers loafers, does not have an interest in tie shoes, or prefers something about the loafers in particular.

The interactive diary may be digital and may include artificial intelligence in addition to or rather than rules based decision making, and such artificial intelligence may be embedded in the personal care device or a remote device.

Thus the present system compiles the information using the interactive diary, either passively (without user input) or actively (e.g. by engaging the user, asking questions based on the action or situation presented), assesses the information generally by category, and makes recommendations or provides information to the user, or solicits additional specific information, in either general instances (e.g. displaying a target heart rate during exercise, displaying prior blood pressure readings when taking blood pressure) or specific instances (when the user is considering buying a brown blouse, indicating such a color generally does not match her skin tone, or when queried by the user, suggesting running four days per week instead of two to achieve a desired health/weight goal). Such functionality may include progressing through logic trees or other logic progressions wherein information is assessed and suggestions or information provided for the benefit of the user.

Health Band

Figure 18:
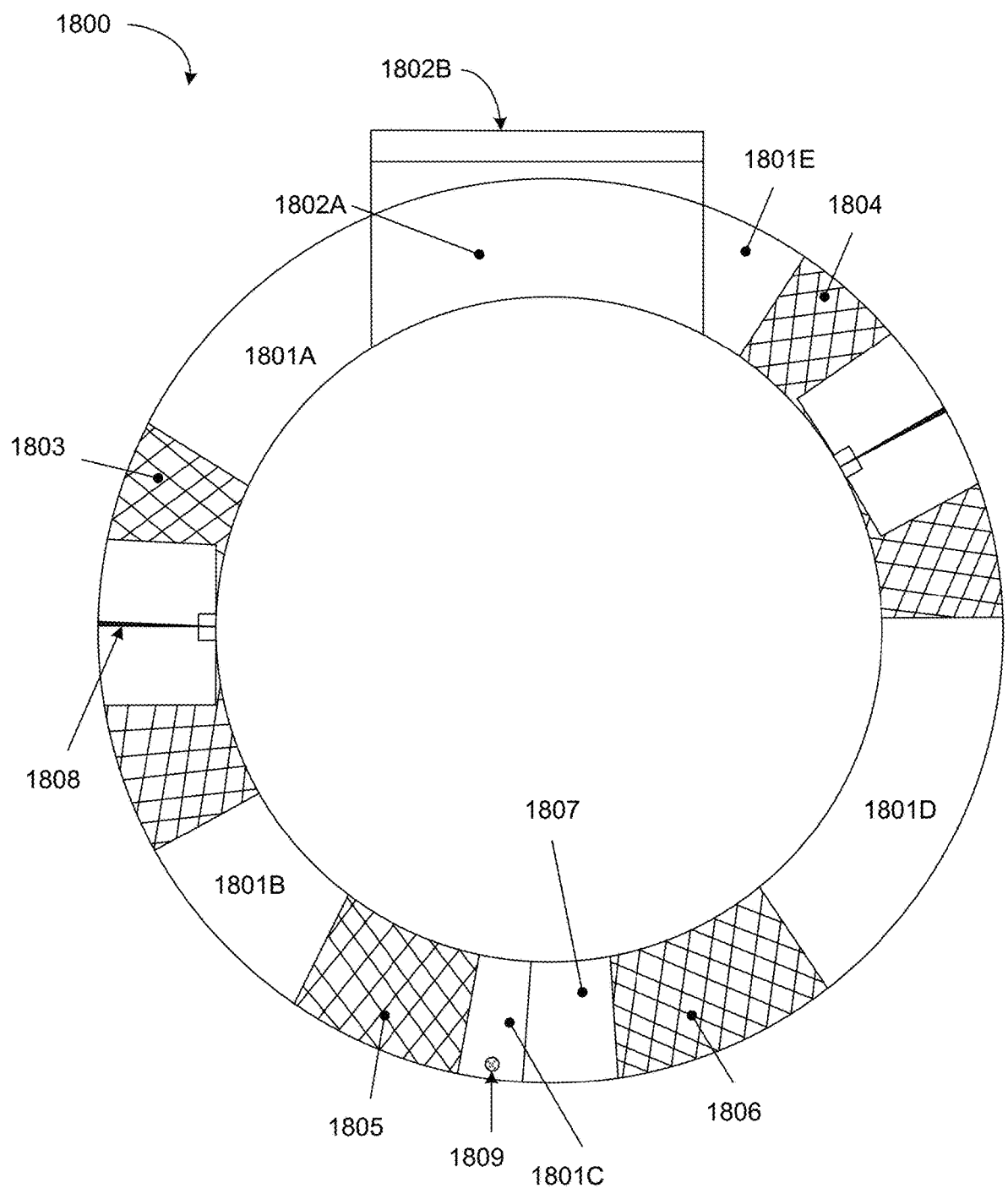
FIG. 18 is an embodiment of the health band design according to the present design.

A further aspect of the present design is provided in FIG. 18. From FIG. 18, there is presented a health band 1800 that may optionally be provided and sized for a finger or a wrist of a person. Parts of the health band 1800, including but not limited to sections 1801A-E, may be formed of a flexible material in order to fit loosely around most persons.

Figure 19:
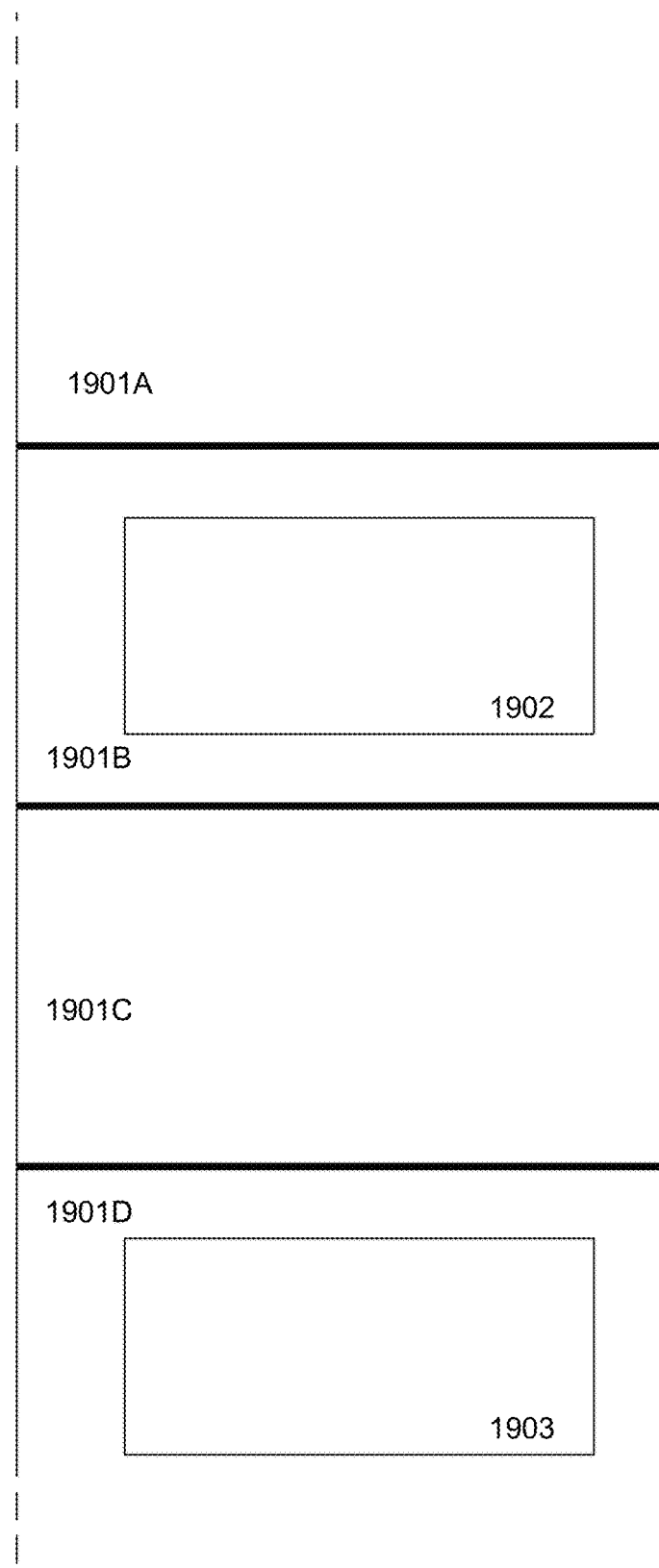
FIG. 19 shows an alternate health band embodiment.

While FIG. 18 is a side view that shows different non-joined flexible material sections or segments, it is to be understood that flexible material may be provided in some or all pieces or segments, where one illustration of a design wherein flexible material is provided in all segments is shown in FIG. 19. FIG. 19 only represents part of the health band, and flexible segments 1901A-D are shown, where segments 1901A and 1901C are essentially completely formed of flexible material, while segments 1901B and 1901D are partially formed from flexible material. Functional units 1902 and 1903 presented, which may be functional units or components such as those shown in FIG. 18 and described below.

From FIG. 18, a processing module 1802A is shown connected in this embodiment to screen 1802B, as well as, inflatable cuffs 1803, 1804, 1805 and 1806, and lock/adjustment element of 1807. Other modules and/or functional components may be provided that facilitate additional patient/user personal sensing functionality, additional transmission or reception or processing functionality, and/or different patient treatment functionality.

Processing module 1802A may include a display screen and hard or soft buttons selectable by the user. Processing module 1802A may further include transmission and reception capability (Wi-Fi, Bluetooth, cellular, and/or any other transmission and reception capability known). Such a device may transmit information to and receive data for the personal care device described herein and/or other remote devices. Data may be transmitted to and received from the cloud directly or indirectly, and the processing module 1802A may be connected in any available and appropriate manner, such as by wire, to the other functional components shown, i.e. the inflatable cuffs. Sensors, such as gyroscopic sensors that sense motion, may also be provided.

Inflatable cuffs 1803, 1804, 1805 and 1806 are simply cuffs or cuff components that are inflatable, inflatable by the user using air or another fluid and may include a valve to receive or expel fluid and may be inflatable in order to fit the user as desired. In FIG. Y, two of the inflatable cuffs 1803 and 1804 include a device such as a V-chip (not shown) and a retractable needle, e.g. retractable needle 1808. A V-Chip is a relatively new technology that is small, in its current form the size of a credit card, and analyzes a blood sample for various maladies. A drop of blood may, for example, indicate a cholesterol level. In general the current V-Chip, developed by Houston Methodist, includes two layers of glass where one layer includes a series of grooves. The other layer of glass includes openings or wells that include different antibodies, lipids, DNA/RNA pieces, and other components such as a catalyst enzyme and a dye. When blood is provided to the grooved side, the sample binds to the material in the wells, and such binding activates the catalase enzyme. Resulting oxygen pushes dye up the channel and the results can be read by a person like a bar chart, or alternately, by a reading device or a dye sensing device. In one embodiment, a material other than dye may be provided that can be sensed by the system in a particular manner—electrically, volumetrically, or otherwise. However, when using the current contemplated V-Chip design, the present design may further include a visual reading component, such as a camera and software configured to determine height of the dye within the grooves provided.

In operation, the inflatable cuff component 1803 or 1804 may employ the needle, for example retractable needle 1808, to extract a drop of blood from the user and may provide that drop of blood to a V-Chip for analysis. Optical analysis of the V-Chip may occur, using an optical sensor (not shown), and results provided to the processing module 1802A. Processing module 1802A may assess the results of the blood extraction and may alternately provide the results to a remote device for analysis.

As may be appreciated, the extraction of blood is carried out in a hygienic manner, potentially including application of alcohol or other appropriate cleaning/sterilizing materials to the user before and/or after extracting blood, and other sterilization techniques may be used as appropriate. Such techniques may require a liquid reservoir and a pressure applicator to apply a liquid, for example, again using connections to processing module 1802A.

A lock and adjustment component 1807 may also be provided enabling attachment, removal, and size adjustment for the health band. Also pictured in this embodiment is a sound sensor or microphone component 1809 used to sense voice commands or other sound attributes, such as alarms. The sound sensor or microphone component 1809 may be connected to processing module 1802A to receive and process sounds sensed, and voice translation functionality may be provided in processing module 1802A. As an example, the user may say "draw blood," such a statement may be received by sound sensor or microphone component 1810 and processed by processing module 1802A to draw blood using inflatable cuff component 1803 and retractable needle 1808.

The health band may be provided for a wrist of a user and may be provided as a ring, and the components may be inflated or substituted with different components to enable the user to wear the device on any finger and/or body parts such as around or near an ankle if desired.

Thus according to the present design, vital signs may be assessed, including heart rate, blood pressure, oxygen saturation, integrity of capillary refill, and temperature, and certain lab work may be performed, such as collection and analysis of blood or sweat, and health and fitness may be monitored.

Portable Dispenser

Figure 20:
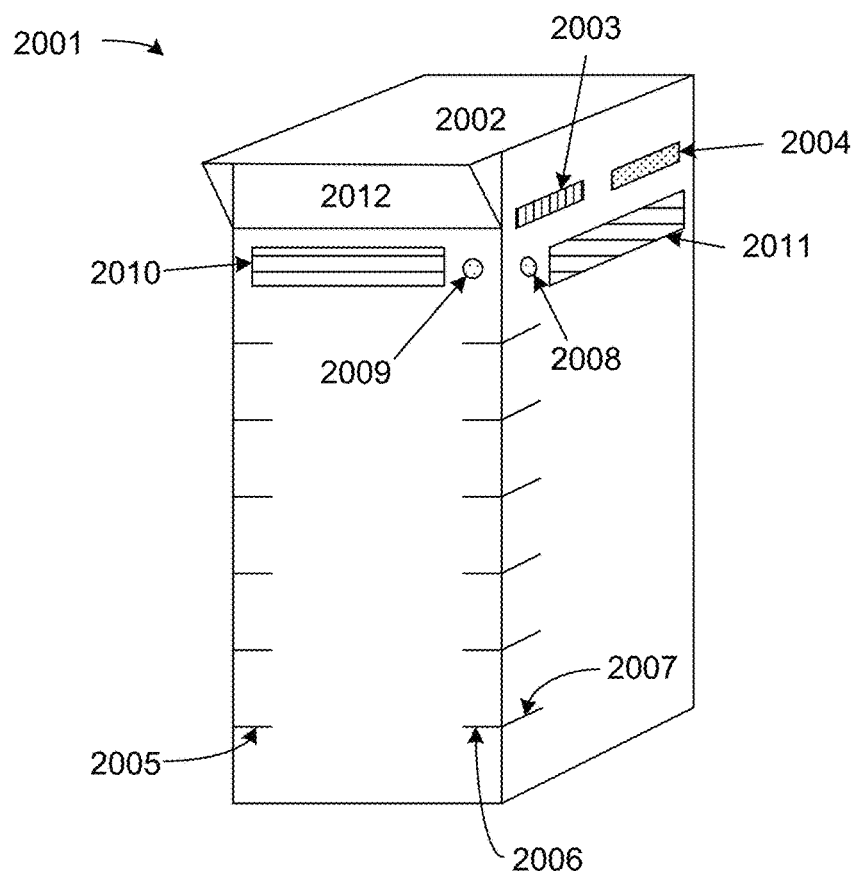
FIG. 20 illustrates a dispenser according to the present design.

An additional aspect of the present design is a portable dispenser, such as a portable pill dispenser, with one representation shown in FIG. 20. From FIG. 20, portable pill dispenser 2001 is generally rectangular in shape but may take different forms or shapes. Screen 2002 may be any type of appropriate screen, including a flexible OLED screen, that displays user specific and pill dispenser specific information. As an example, the screen 2002 may display an indication that the user is to take his/her pills, may display information such as the number of pills contained, reminders to renew prescriptions, and other related information. Alternately or in addition, non-pill dispenser relevant information may be provided on screen 2002, and the pill dispenser may be electronically or wirelessly or otherwise connected to a personal care device as disclosed herein. As an example, news, advertisements, or other desired information may be provided to screen 2002 of portable pill dispenser 2001.

Portable pill dispenser 2001 includes processor 2003 and a transmitter, such as transmitter 2004, connected to processor 2003 and configured to communicate (transmit/receive) to a remote device or devices, such as a personal care device as disclosed herein or a central server. The processor 2003 may transmit and receive communications in any appropriate manner, including but not limited to Bluetooth, WiFi, cellular/wireless, and may be connected to the internet/cloud to provide or receive information. For example, when the user receives and presumably takes a pill or medicine, the information (pill, time taken, and other relevant information) may be transmitted to a personal care device as disclosed herein or a central server, or to the cloud for storage and subsequent retrieval by the device or another appropriate device.

Also shown in FIG. 20 is an arrangement of levels, shown by markings 2005 through 2007 in this view. Any number of levels may be provided, depending on height of the portable pill dispenser 2001. Markings 2005 through 2007 represent positions where the top or the bottom of a prescription tray may be positioned, and may be one of a number of such positions, which may be physically marked or merely represent the desired position of the prescription tray(s) described below. Microphones 2008 and 2009 and speakers 2010 and 2011 may also be provided, and more or fewer microphones and speakers may be provided, to receive voice commands or other sounds and may be connected to processor 2003 for processing received voice commands or sounds, such as "give me my next pills" or otherwise. Speakers 2010 and 2011 may provide sounds advising the user of relevant information, such as "time to take your noon pills" or otherwise. Also shown in this view is serving drawer 2012, used to provide the user with a prescription tray as described below. Power unit 2013 may be a self contained power unit, such as including batteries to drive the spring or ratchet device and power the prescription tray out serving drawer 2012. Alternately or additionally, a power or charging cord 2014, shown as an optional dotted line, may be employed to power the dispenser 2001.

Figure 21:
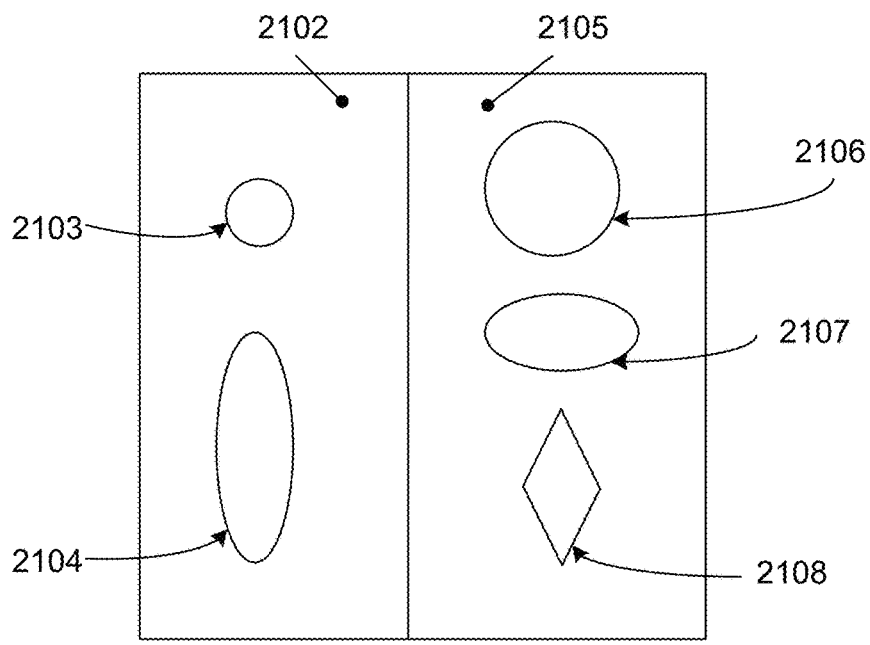
FIG. 21 is a prescription tray according to one embodiment of the present design.

FIG. 21 illustrates one embodiment of a prescription tray 2101 according to the present design. The prescription tray 2101 may take different forms, and may be produced from any appropriate material, including but not limited to plastic, production by a 3D printer, metal, composite, compressed paper, or biodegradable material. In the prescription tray 2101 shown in FIG. 21, two halves are presented, left half 2102 including two slots 2103 and 2104 and right half 2105 including three slots 2106, 2107, and 2108. Each slot in left half 2102 and right half 2105 is intended for consumption by the user/patient at a particular time in the day, such as left half 2102 from noon to midnight, and right half 2105 from midnight to noon. More or fewer sections may be provided, including a single section in the tray rather than the two shown, depending on the user and the medications provided. In certain instances, more than one prescription tray 2101 may be needed and may be provided in a prescribed order, e.g. morning prescriptions first in a first prescription tray and evening prescriptions second in a second prescription tray. Information may be printed on the prescription tray 2101, such as the prescription name, time the prescription should be taken, user name, and/or other relevant information.

The slots 2103, 2104, 2106, 2107, and 2108 are preferably sized for the prescription provided and may receive or include the pill or drug within an opening or slot in the prescription tray 2101. While described herein as prescriptions, virtually anything may be provided, including consumables such as vitamins, aspirin, supplements, etc. While called a "pill dispenser" herein, it is to be understood that the present design is not limited to pills and may dispense any appropriate product or item. And while solid pills are contemplated, the design is not so limited; materials such as liquids may be provided with an appropriate cover, e.g. a plastic cover over the liquid contained in a slot, and multiple pills or items may be provided within a slot, and slots may take different forms depending on circumstances.

In the case of a 3D printer, the prescription tray 2101 may be printed based on a computerized database of size and shape of the pill or item, with appropriate size buffer provided, e.g. 1 mm on each side more than the size of the pill in question.

In the embodiment of FIG. 20 there is provided a mechanism that advances each prescription tray at a desired time or under desired circumstances. In a situation where the user is a responsible adult and no children are of concern, the pill dispenser 2001 may simply advance each prescription tray in order, using for example a spring mechanism (not shown) that pushes the stack of prescription trays upward for removal from the serving drawer 2012. Alternately, a spring type mechanism may be provided with a timer, or another advancement mechanism, such as a ratcheting mechanism, may be provided such that prescription trays advance only at a desired time. In all instances, the prescription tray, when advanced, is removed via serving drawer 2012, and the serving drawer 2012 may be mechanically provided to push the tray out from the pill dispenser 2001 at an appropriate time, using a force member driven by the processor 2003 provided. Timing of advancement may be provided by processor 2003, e.g. it is now midnight and a next prescription tray should be advanced, commanding a release of a spring or other mechanical advancement and possibly ejecting a next prescription tray from the serving drawer 2012.

FIG. 22 shows a further representation of the dispenser embodiment, including a version of the dispenser 2201 with prescription trays represented as stacked therein, and a second version of the dispenser 2202 with one prescription tray 2203 being ejected and the delivery drawer 2204 opened and not shown in the dispenser 2202 representation as it has been flipped downward. Thus the delivery drawer 2204 may be hinged or alternately retracted. In these embodiments, a photo cell (not shown) may be employed in association with a processing module to determine whether and when the tray is received by the user.

Thus the present design further provides a dispenser, such as a pill dispenser, that facilitates providing prescriptions or other consumables at desired times or under desired conditions, with an ability to interface with the personal care device and system disclosed herein.

Thus the present design may include hardware and devices configured to facilitate personal care of a user. Personal care and other functionality may be provided in, for example, the areas of health, fitness, wellness, fashion, cosmetics, and/or pharmaceuticals. The system may include a device configured to receive personal health related modules, which are interchangeable, and may include a device having a mirror or reflective surface that acts as a computing device display. The device may include processing and data storage capabilities, and the user may freely exchange personal care modules as desired. The device may collect information and may provide the information to a remote device arrangement, including but not limited to the internet "cloud" and may process the information received. As an example, information regarding a desired weight goal may be provided, and health recommendations may be transmitted from the remote device arrangement to the device and the user. A handheld unit configured to receive information and possibly process the information may be provided so that the user may take the handheld unit with her to a remote location. Information for multiple devices may be maintained at the remote device arrangement, and differing levels of service may be provided. An interactive diary may be provided that tracks attributes of each user and may process data to provide recommendations and information as appropriate to the user, determined specifically for the user according to his or her personal data collected over time in the areas of health, fitness, wellness, fashion, cosmetics, and/or pharmaceuticals. A health band and/or pill dispenser may also be provided.

Thus the present design may include a dispenser apparatus comprising a central opening, a display, an advancing mechanism configured to advance at least one prescription tray vertically through the central opening of the dispenser apparatus, and an ejection mechanism configured to eject one prescription tray from the dispenser apparatus.

Alternately, the present design may comprise a prescription tray dispensing apparatus comprising an outer enclosure surrounding a central opening, the outer enclosure sized to accommodate a prescription tray, a display, an advancing mechanism configured to advance the prescription tray vertically through the central opening within the outer enclosure of the prescription tray dispensing apparatus, and an ejection mechanism configured to eject the prescription tray from the prescription tray dispensing apparatus.

A further embodiment of the present design comprises a dispenser apparatus configured to interface with a personal care system, the dispenser apparatus comprising an enclosure surrounding a central opening, a display, an advancing mechanism configured to advance at least one prescription tray vertically through the central opening of the dispenser apparatus, and an ejection mechanism configured to eject one prescription tray from the dispenser apparatus. The personal care system comprises a personal care combination display/mirror device comprising a surface operating as a reflective surface and a plurality of connection ports, each connection port configured to receive a hardware personal care module, each hardware personal care module comprising software facilitating performance of at least one personal care function and configured to interact with the personal care combination display/mirror device to facilitate personal care of a user, wherein personal care comprises at least one of health, fitness, wellness, fashion, cosmetics, and pharmaceuticals.

The foregoing description of specific embodiments reveals the general nature of the disclosure sufficiently that others can, by applying current knowledge, readily modify and/or adapt the system and method for various applications without departing from the general concept. Therefore, such adaptations and modifications are within the meaning and range of equivalents of the disclosed embodiments. The phraseology or terminology employed herein is for the purpose of description and not of limitation.

What is claimed is:

1. A dispenser apparatus, comprising:
   four joined vertically oriented sides, the four joined vertically oriented sides forming a single vertically oriented central opening therein;
   a plurality of vertically stacked prescription trays, wherein a first prescription tray of the plurality of vertically stacked prescription trays contains a first combination of prescriptions and a second prescription tray of the plurality of vertically stacked prescription trays contains a second combination of prescriptions differing from the first combination of prescriptions, each combination of prescriptions to be received and subsequently taken by a patient at a predetermined time, wherein the first prescription tray comprises medications to be taken first in time, the second prescription tray comprises further medications to be taken second in time, and all subsequent prescription trays are vertically ordered for medications contained therein to be taken at successively later times;
   an advancing mechanism configured to advance the plurality of vertically stacked prescription trays sequentially in a vertical direction through the single vertically oriented central opening of the dispenser apparatus;
   an ejection mechanism comprising a force element configured to eject only a topmost vertically stacked prescription tray from the dispenser apparatus horizontally through a serving drawer opening, wherein the ejection mechanism ejecting the topmost vertically stacked prescription tray causes the advancing mechanism to advance a next vertically stacked prescription tray upward through the single vertically oriented central opening to be in line with the force element and serving drawer opening; and
   a processor configured to cause the ejection system mechanism to advance the next vertically desired prescription tray at a prescription tray desired advancement time based on the predetermined time all prescriptions provided therein should be received and subsequently taken by the patient;
   receive information from a remote device for display on a display, wherein the remote device is configured to transmit user personal care communications personalized to the user to and receive user personal care communications personalized to the user.

2. The dispenser apparatus of claim 1, wherein the remote device comprises a personal care display and a plurality of connection ports, each connection port configured to receive a hardware personal care module, each hardware personal care module comprising software facilitating performance of at least one personal care function and configured to interact with the personal care display to facilitate personal care of a user, wherein personal care comprises at least one of health, fitness, wellness, fashion, cosmetics, and pharmaceuticals.

3. The dispenser apparatus of claim 2, wherein the personal care display is further configured for the user to freely substitute selected and different hardware personal care modules in the plurality of connection ports.

4. The dispenser apparatus of claim 3, wherein the personal care display is further configured to maintain an interactive diary for the user, the interactive diary configured to collect information regarding personal care assessed for the user over a period of time such that the apparatus may determine and selectively provide suggested actions to be taken by the user based on the assessment.

5. The dispenser apparatus of claim 1, further comprising a processor, at least one speaker, and at least one microphone, each speaker and microphone configured to provide audio information and receive audio information, respectively.

6. The dispenser apparatus of claim 1, wherein the prescription tray is formed for one user and includes prescriptions or products to be ingested by the one user.

7. The dispenser apparatus of claim 1, wherein the advancing mechanism and the spring are configured to selectively advance at least one prescription tray by one prescription tray height through the single vertically oriented central opening.

8. The dispenser apparatus of claim 6, where the prescription tray comprises one selected from a group consisting of plastic and a 3D printed tray.

9. A prescription tray dispensing apparatus, comprising:
   an outer enclosure formed of four vertically edge joined sides, the outer enclosure having a single vertically oriented central opening therein, the outer enclosure sized to accommodate a prescription tray;
   a plurality of vertically stacked prescription trays, wherein a first prescription tray of the plurality of vertically stacked prescription trays contains a first combination of prescriptions and a second prescription tray of the plurality of vertically stacked prescription trays contains a second combination of prescriptions differing from the first combination of prescriptions, each combination of prescriptions to be received and subsequently taken by a patient at a predetermined time, wherein the first prescription tray comprises medications to be taken first in time, the second prescription tray comprises further medications to be taken second in time, and all subsequent prescription trays are vertically ordered for medications contained therein to be taken at successively later times;

an advancing mechanism configured to advance the plurality of vertically stacked prescription trays sequentially in a vertical direction through the single vertically oriented central opening within the outer enclosure of the prescription tray dispensing apparatus;

an ejection mechanism comprising a force element configured to eject only a topmost vertically stacked prescription tray from the prescription tray dispensing apparatus horizontally through a serving drawer opening, wherein the ejection mechanism ejecting the topmost vertically stacked prescription tray causes the advancing mechanism to vertically advance a next vertically stacked prescription tray upward through the single vertically oriented central opening to be in line with the force element and serving drawer opening; and a processor configured to cause the ejection system mechanism to advance the next vertically desired prescription tray at a prescription tray desired advancement time based on the predetermined time all prescriptions provided therein should be received and subsequently taken by the patient;

receive information from a remote device for display on a display, wherein the remote device is configured to transmit user personal care communications personalized to the user to and receive user personal care communications personalized to the user.

10. The prescription tray dispensing apparatus of claim 9, wherein the remote device comprises a personal care display and a plurality of connection ports, each connection port configured to receive a hardware personal care module, each hardware personal care module comprising software facilitating performance of at least one personal care function and configured to interact with the personal care display to facilitate personal care of a user, wherein personal care comprises at least one of health, fitness, wellness, fashion, cosmetics, and pharmaceuticals.

11. The prescription tray dispensing apparatus of claim 10, wherein the personal care display is configured for the user to freely substitute selected and different hardware personal care modules in the plurality of connection ports.

12. The prescription tray dispensing apparatus of claim 11, wherein the personal care display is further configured to maintain an interactive diary for the user, the interactive diary configured to collect information regarding personal care assessed for the user over a period of time such that the apparatus may determine and selectively provide suggested actions to be taken by the user based on the assessment.

13. The prescription tray dispensing apparatus of claim 9, further comprising a processor, at least one speaker, and at least one microphone, each speaker and microphone configured to provide audio information and receive audio information, respectively.

14. The prescription tray dispensing apparatus of claim 9, wherein each prescription tray is formed for one user and includes prescriptions or products to be ingested by the one user.

15. The prescription tray dispensing apparatus of claim 9, wherein the advancing mechanism and the spring are configured to selectively advance at least one prescription tray by one prescription tray height through the single vertically oriented central opening.

16. A dispenser apparatus configured to interface with a personal care system, the dispenser apparatus comprising:
an enclosure comprising four joined sides forming a single vertically oriented central opening therein;
a plurality of vertically stacked prescription trays, wherein a first prescription tray of the plurality of vertically stacked prescription trays contains a first combination of prescriptions and a second prescription tray of the plurality of vertically stacked prescription trays contains a second combination of prescriptions differing from the first combination of prescriptions, each combination of prescriptions to be received and subsequently taken by a patient at a predetermined time, wherein the first prescription tray comprises medications to be taken first in time, the second prescription tray comprises further medications to be taken second in time, and all subsequent prescription trays are vertically ordered for medications contained therein to be taken at successively later times;
an advancing mechanism configured to advance the plurality of vertically stacked prescription trays sequentially in a vertical direction through the single vertically oriented central opening of the dispenser apparatus;
an ejection mechanism comprising a force element configured to eject only a topmost vertically stacked prescription tray from the dispenser apparatus horizontally through a serving drawer opening, wherein the ejection mechanism ejecting the topmost vertically stacked prescription tray causes the advancing mechanism to vertically advance a next vertically stacked prescription tray upward through the single vertically oriented central opening to be in line with the force element and serving drawer opening; and
a processor configured to cause the ejection system mechanism to advance the next vertically desired prescription tray at a prescription tray desired advancement time based on time all prescriptions provided therein should be received and subsequently be taken by the user;
wherein the personal care system comprises a personal care display and a plurality of connection ports, each connection port configured to receive a hardware personal care module, each hardware personal care module comprising software facilitating performance of at least one personal care function and configured to interact with the personal care display to facilitate personal care of a user, wherein personal care comprises at least one of health, fitness, wellness, fashion, cosmetics, and pharmaceuticals,
receive information from the personal care system for display on a display, wherein the personal care system is configured to transmit user personal care communications personalized to the user to and receive user personal care communications personalized to the user.

17. The dispenser apparatus of claim 16, wherein the personal care display is configured for the user to freely substitute selected and different hardware personal care modules in the plurality of connection ports.

18. The dispenser apparatus of claim 16, wherein each prescription tray comprises one selected from a group consisting of plastic and a 3D printed tray formed to accept a prescription or product for ingestion for a specific individual.

* * * * *